United States Patent [19]
Baker

[11] Patent Number: 5,843,990
[45] Date of Patent: Dec. 1, 1998

[54] PYRAN-CHROMENONE COMPOUNDS, THEIR SYNTHESIS AND ANTI-HIV ACTIVITY

[75] Inventor: David Baker, Knoxville, Tenn.

[73] Assignee: The University of Tennessee Research Corporation, Knoxville, Tenn.

[21] Appl. No.: 772,764

[22] Filed: Dec. 23, 1996

Related U.S. Application Data

[63] Continuation-in-part of Ser. No. 395,035, Feb. 27, 1995, Pat. No. 5,608,085.
[51] Int. Cl.[6] .................................................. A61K 31/35
[52] U.S. Cl. ............................................ 514/455; 549/282
[58] Field of Search .............................. 549/282; 514/455

[56] References Cited

PUBLICATIONS

Galinis, D. L., et al., Structure–Activity Modifications of the HIV–1 Inhibitors(+)–Calanolide A and (−)–Calanolide B[1], *J. Med. Chem.* 1996, 39, 4507–4510.
Rehder, K. S., et al., Synthesis of [12-$^3$H]–(+)–Calanolide A, *Journal of Labelled Compound and Radiopharmaceuticals* vol. XXXVIII, No. 12, 1996, 1077–1081.
Zembower, D. E., et al., Structural Analogues of the Calanolide Anti–HIV Agents. Modification of the trans–10, 11–Dimethyldihydropyran–12–olRing (Ring C)[1], *J. Med. Chem.* 1997, 40, 1005–1017.
Taylor, P. B., et al., Kinetic and Mutational Analysis of Human Immunodeficiency Virus Type 1 Reverse Transcriptase Inhibition by Inophyllums, a Novel Class of Non–nucleoside Inhibitors, *The Journal of Biological Chemistry*, 1994, 269, 6325–6331.
Stout, G. H., et al., The Structure of Costatolide, *J. Org. Chem.*, 1964, 29, 3604–3609.
Kashman, Y., et al., *J. Med. Chem.*, 1992, 35, 2735–2743.
Chenera, B., et al., *J. Org. Chem.*, 1993, 58, 5605–5606.
Fuller, R. W., et al., *Bioorg. Med. Chem. Lett.*, 1994, 4, 1961–1964.
Newman, R. A., et al., *J. Chromatogr. B.*, 1994, 658, 129–133.
Kawazu, K., et al., *Bull Chem. Res.*, Kyoto Univ, 1972, 50, 160–167; Chem. Abstr. 78:13744.
Patil, A.D., et al., *J. Med. Chem.*, 193, 36, 4130–4138.
Polonsky, J., *Bull. Soc. Chim. Fr.*, 1956, 914–922.
Polonsky, J., et al., *Bull. Soc. Chim. Fr.*, 1958, 929–944.
Rao, A. V. R., et al., *Tetrahedron Lett.*, 1994, 35, 6347–6350.
Deshpande, P. P., et al., A Single Approach to the Synthesis of the Chiral Substituted Chroman Ring of Calophyllum Coumarins, *synth:w95:w61*, 1995.
Deshpande, P. P., et al., Synthesis of Optically Active Calonolides A and B, *J. Org. Chem.*, 1995, 60, 2964–2965.
Baker, D. C., et al., Synthesis of Enantiomerically Pure Drugs From Sugars, Abstract No. 75, Presented at 29th ACS Middle Atlantic Regional Meeting, May 24–26, 1995.

Spence, Rebecca A., et al., Mechanism of Inhibition of HIV–1 Reverse Transcriptase by Nonnucleoside Inhibitors, *Science*, 1995, 267, 988–993.
Enger, C., PhD., et al., Survival From Early, Intermediate, and Late Stages of HIV Infection, Abstract, *JAMA*, 1996, 275, 1329–1334.
Kawazu, K., et al., The Piscicidal Constituents of Calophyllum Inophyllum Linn., *Tetrahedron Letters*, 1968, 19, 2383–2385.
Rehder, K. S., et al., Total Synthesis of (+)–Calanolide A, *Synthetic Communications*, 1996, 26(21), 4005–4021.
Ishikawa, T., et al., Cesium Fluoride–Induced Intramolecular Michael Addition: Highly Diastereoselective Ring Construction of a trans–2,3–Dimethylchroman–4–one, *J. Org. Chem.*,1996, 61, 6484–6485.
Khilevich, A., et al., Synthesis of (+)–Calonide, A, An Anti–HIV Agent, Via Enzyme–Catalyzed Resolution Of The Aldol Products, *Tetrahedron: Asymmetry*, 1996, 7(11), 3315–3326.
McKee, Tawnya C., et al., New Pyranocoumarins Isolated from *Calopyllum lanigerum* and *Calophyllum teysmannii*, *J. Nat. Prod.*, 1996, 59, 754–758.
Khilevich, A., et al., A Versatile Approach For Synthesis Of 2,3–Dimethyl Chroman–4–Ones, Intermediate For Calanolide Anti–HIV Agents, Via Aldol/Mitsunobu Reactions, *Synthetic Communications*, 1996, 26(20), 3757–3771.
Currens, M. J., et al., Abstract, Kinetic analysis of inhibition of human immunodeficiency virus type–1 reverse transcriptase by Calanolide A, *Journal of Pharmacology and Experimental Therapeutics*, 1996, 279, 652–661.
Currens, M. J., et al., Abstract, Antiviral activity and mechanism of action of Calanolide A against the human immunodeficiency virus type–1, *Journal of Pharmacology and Experimental Therapeutics*, 1996, 279, 645–651.
Hammer, S. M., et al., A Controlled Trial of Two Nucleoside Analogues Plus Indivavir In Persons With Human Immunodeficiency Virus Infection and CD4 Cell Counts Of 200 Per Cubic Millimeter Or Less, Abstract, *The New England Journal of Medicine*, 1997, 337, 725–733.
Gulick, R. M., et al., Treatment With Indinavir, Zidovudine, And Lamivudine In Adults With Human Immunodeficiency Virus Infection And Prior Antiretroviral Therapy, Abstract, *The New England Journal of Medicine*, 1997, 337, 734–739.
Buckheit, R. W., et al., Abstract, A diarylsulphone non–nucleoside reverse transcriptase inhibitor with a unique sensitivity profile to drug–resistant virus isolates, *Antiviral Chemistry & Chemotherapy*, 1996, 7, 243–252.
Ohta, Y. and Shinkai, Ichiro, New Drugs—Reports of New Drugs Recently Approved by the FDA, Lamivudine, *Bioorganic & Medicinal Chemistry*, 1997, 5, 639–640.

*Primary Examiner*—Amelia Owens
*Attorney, Agent, or Firm*—Weiser and Associates, P.C.

[57] ABSTRACT

The invention relates to pyran-chromenone compounds, their synthesis and anti-HIV activity. Methods of synthesis are disclosed; the compounds have activity against reverse transcriptase. Biological compositions containing the compounds and method of treating patients are also disclosed.

33 Claims, 3 Drawing Sheets

$R^1$ is iosopropyl, methyl, sec-butyl, allyl or propargyl; $R^2$ is 1-propyl; $R^3$ is hydroxyl or keto R[1] is isopropyl, methyl, sec-butyl, allyl or propargyl; R[2] is 1-propyl; R[3] is hydroxyl or keto R[1] is iosopropyl, methyl, sec-butyl, allyl or propargyl; R[2] is 1-propyl; R[3] is hydroxyl or keto

PYRAN-CHROMENONE COMPOUNDS, THEIR SYNTHESIS AND ANTI-HIV ACTIVITY

RELATED APPLICATIONS

This application is a continuation-in-part of application Ser. No. 08/395,035, filed Feb. 27, 1995 allowed, now U.S. Pat. No. 5,608,085 issued on Mar. 4, 1997. Said parent application (parent application) is explicitly incorporated herein by reference in its entirety.

The work in conjunction with this invention was supported, in part, by contracts NO1-CM-17551 and -47038 from the Drug Synthesis and Chemistry Branch, Developmental Therapeutics Program of the National Cancer Institute.

1. Field of the Invention

The present invention relates to compounds which inhibit retrovical infection. The invention also relates to the synthesis of these compounds and their use in clinical applications, such as antiviral therapy. More specifically, this invention relates to certain chromenone derivatives which have antiviral activity.

2. Background of the Invention

The calanolides have been identified as potent, active agents that are effective inhibitors[1] of the human immunodeficiency virus (HIV), which is generally accepted as the causative agent for acquired immunodeficiency deficiency syndrome (AIDS) in humans.[2]

There are several ways in which an agent can exhibit anti-retroviral activity. For example, HIV requires at least four viral proteins for replication: reverse transcriptase (RT), protease (PR), transactivator protein (TAT), and regulator of virionprotein expression (REV). Accordingly, viral replication could theoretically be inhibited through inhibition of any one or all of the proteins involved in viral replication. Examples of viruses that may be treated in accordance with the present invention include, but are not limited to, Type C and Type D retroviruses, HTLV-1, HTLV-2, HIV, FLV, SIV, MLV, BLV, BIV, equine infectious, anemia virus, avian sarcoma viruses, such as rous sarcoma virus (RSB), hepatitis type A, B, non-A and non-B viruses, herpes viruses, cytomegaloviruses, influenza viruses, arboviruses, varicella viruses, measles, mumps and rubella viruses.

A process for the total synthesis of calanolides A and B, as well as their enantiomers, is the subject of the parent patent application identified above and a publication in the chemical literature.[3] (+)-Calanolide A and (−)-calanolide B have been identified as the more potent diastereomers in this class of compounds.

In further work, in all effort to identify compound analogues which have the desirable properties of drug delivery, stability, water and organic solvent solubility and other desirable properties and yet retain or exceed the antiviral, specifically the anti-HIV potency of the drugs disclosed in the parent application, a group of compounds was unexpectedly discovered in which the structure in comparison with the known coumarin derivatives like the calanolides (or related molecules like the inophyllums), is devoid of the chromene ring, specifically, the 6,6-dimethyl-2H-pyran ring-fused 2,3-f as in the parent patent application. That a compound of such a structure would exhibit antiviral activity, as was discovered in accordance with the invention, was unexpected. This is because as far as is known, this class of antiviral non-nucleoside which have been identified in the prior art as potent inhibitors of human immuno deficiency virus-1 reverse transcriptase (HIV-1 RT) are all characterized by the presence of a chromene ring, which the compounds of the invention do not possess.

Several publications disclose compounds stated to have antiviral activity, and all possess a chromene ring.[4]

THE COMPOUNDS OF THE INVENTION

The compounds of the invention have in the 5- position of the coumarin ring (which corresponds to the 6- position on calanolides) an oxygen atom to which are linked substituents, which are further defined below. In position C-4 on the coumarin ring (which also corresponds to the 4-C position in calanolides), the substitutents ray be any substituents which have been described as suitable for calanolides and derivatives, although some substituents further defined below are preferred. Substituents in the 8-, 9- and 10-positions of the compounds of the invention (which corresponds to positions 10-, 11- and 12-, respectively in the calanolides) are also defined further below.

SUMMARY OF THE INVENTION

The invention provides new heterocyclic compounds having biological activity, particularly antiviral activity. In particular, the invention provides several series of diastereoisomers, including several pairs of enantiomers. The invention includes the pharmaceutically active salts of the compounds.

The invention also provides optically active compounds of very high optical purity. The compounds are active in tests of retroviral activity and of particular interest are those of remarkable potency as inhibitors of the human immunodeficiency virus (HIV).

Of particular interest from the point of view of anti-HIV activity are within a group of four optical isomers, two of which have a particularly potent and broad spectrum of anti-HIV activity.

The invention also provides biologically active compositions which comprise one or more of the compounds of the invention in an effective, nontoxic amount in combination with a pharmaceutically acceptable carrier.

Another particularly interesting embodiment of the invention is the property of the compounds of the invention as chemotherapeutic agents for controlling and limiting the proliferation of various strains of HIV virus that have been shown to be resistant to TiBO and to other nucleoside or non-nucleoside anti-HIV agents, such as AZT, ddI, d4T, ddC, nevirapine and others. Thus, the invention provides for compositions and combination regiments where the antiviral compounds of the invention are administered together with other anti-HIV agents and/or sequentially prior or thereafter.

The invention also provides for a drug combination of HIV protease inhibitors like ritonavir, saquinavir mesylate and others.

In still another aspect, the invention provides a method for treating a mammal, particularly a human, infected with a retro-virus, which comprises administering to said mammal in need of such treatment an effective, nontoxic amount of the compound(s) of the invention.

The invention also relates to a process for synthetically preparing the compounds of the invention in accordance with several variants which are described further herein below.

The invention further relates to another class of new compounds which are synthesized in the synthesis of the compounds of the invention. These compounds are useful in ways described hereinafter.

In yet another important aspect, the invention provides for a process for synthetically preparing optically active compounds of the invention in a degree of high purity, that is more than 95% and generally greater than 98% optically pure and free of the corresponding enantiomer.

The invention also relates to racemic mixtures comprising the compounds of the invention and to a method for separating the racemic mixtures into the pairs of optically pure enantiomers.

Other embodiments of the invention will become apparent in the further description of the invention.

The method of the invention comprises, in a general manner, synthesizing the optically active pyran derivatives from an appropriate starting reactant, as described hereinafter. A suitable starting reactant is a formylated coumarin lactone which is then alkylated (or otherwise modified as described hereinafter) at the phenolic hydroxyl group. The alkylated compound is reacted with preferably an optically active organoborane to yield sterogenically defined molecules, having a substitution (designated as $R^3$), such as a C-10 hydroxyl and a C-9 methyl functional group, and after oxidation of the boron-carbon bond to obtain the homallylic alcohol adduct and monosilylating the alcohol to obtain the monosilylated orthoalkenylphenol, causing mercury assisted ring closure to the fused pyran-chromenone. After reduction of the organomercury intermediate, there is obtained the silyl protected derivative, which upon removing the silyl ether protecting group yields the (+)-pyran-chromenone B, with trans, cis relative stereochemistry at C-8, C-9 and C-10, thus the 8R, 9S, 10R stereoisomer B. Epimerization of the C-10 substituents, when $R^3$ is hydroxyl, yields the 8R, 9S, 10S(−)-pyran-chromenone A.

A variant of the synthesis of the invention comprises reacting monosilylated orthoalkenylhomoallelic phenol obtained from the alkylated derivative formylated coumarin C-5 lactone, with an appropriate chriral allyl borane, then causing ring closure as disclosed above, alkylating at the 9-C to yield trans-9,10-dimethylpyranone of type 11, followed by reduction of the pyranone to yield the 10OH(+)-pyran-chromenone (+)-8 as described above.

By selecting an organoborane or equivalent compound of (−)-optical rotation, the (−)- set of chromenone-pyran enantiomers are obtained.

The method of the invention also provides an alternative, ring closure, as described below, on an acyclic keto compound obtained in a known manner. The cyclized keto intermediate is reduced to the desired product.

The pyran-chromenones of the invention may be represented by the following general formulae.

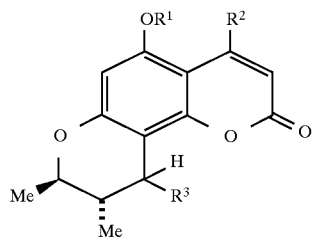

(+)-Calanolide A Analogues

Formula 1

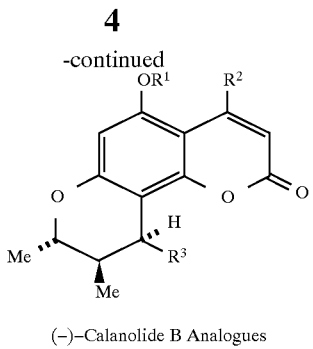

(−)-Calanolide B Analogues

In the compounds of the invention, in the stereoisomers identified as the (+)-A series, the 9-methyl group (indicated by a ⦙⦙⦙ bond) extends below the plane of the paper away from the reader, the 8-methyl and the 10-$R^3$ (indicated by a ◀ bond, respectively, extends above the plane of the paper towards the reader. A typical compound is the (+)-8 compound where $R^3$ is —OH.

In the stereoisomers identified as the (−)-B series, the 9-methyl group and the 10-$R^3$, indicated by a ◀ bond extends, respectively, above the plane of the paper toward the reader, the 8-methyl indicated by a ⦙⦙⦙ bond extend below the plane of the paper away from the reader. A typical compound is the (−)-7 compound where $R^3$ is —OH.

In the compounds of the shown formulae, $R^1$ may be alkyl of either a linear or branched carbon chain preferably not exceeding six carbon atoms, such as methyl, ethyl, propyl, butyl, pentyl, hexyl; 1-methylethyl, 1-methylpropyl, 1,1-dimethylethyl, 1,2-dimethylpropyl. 1,1-dimethylpropyl, 2-methylpropyl, 3-methylbutyl, 4-methylpentyl, 2,2-dimethylpropyl and 1,1-dimethylpentyl; cycloalkyl, having a ring of preferably not more than eight carbon atoms, such as cyclohexyl, 1-cyclohexyl, cyclopentyl, cyclooctyl; or arylalkyl or alkylaryl having a linear or branched alkyl of preferably no more than six carbon atoms and a substituted or unsubstituted aryl or heteroaryl ring system, for example, but not limited to, benzyl, methylphenyl, phenylmethyl, naphthalenyl, piperidinyl, or other cyclic structures, unsaturated hydrocarbons like 2-propenyl, 2-propynyl, 1-methylethenyl and 3-methyl-1-butenyl. The hydrocarbon chains and/or aryl moieties can be substituted with various functional groups, including, but not limited to, —OH, —SH, —OR, —SR, —CONH$_2$, —NH$_2$, —NHR, —NR$_2$ (wherein the Rs are alkyl, cycloalkyl, or arylalkyl) and halogen, such as chlorine or bromine.

$R^2$ can be hydrogen, alkyl of either a linear or branched carbon chain, preferably not more than 6 carbon atoms, cycloalkyl or aryl where, if substituted, the substituents are as described above, and moreover when $R^2$ is aryl, the compound can be an inophyllum analogue.

Substitutions on the alkyl chains and/or the ring systems may include, but are not limited to, —OH, —OR, —SH, —SR, —NH$_2$, —NHR, —NR$_2$, and halogen, such as chlorine and bromine. $R^1$ and $R^2$ may be varied in any combination.

Preferably, $R^2$ is an alkyl group of 1 to 4 carbon atoms, most preferably propyl.

$R^3$ may be hydrogen, hydroxyl, keto (without the H-10), thio, alkyl, alkoxy, ester, fluoro, azido, amino, wherein the alkyl (the alk- of alkoxy) and ester are preferably of lower alkyl.

Amongst the compounds represented by the formula above, those which are presently preferred are those in which $R^1$ is a branched alkyl structure, preferably an iso-alkyl structure, such as isopropyl.

The presently preferred combination is where $R^1$ is 2-propyl, $R^2$ is 1-propyl and $R^3$ is hydroxyl.

It is conceivable that the methyl group on the 8-C and/or 9-C could be a different substituent as from those described herein providing, however, that the compound retain its biological activity.

The invention also relates to the salts of the basic or acid derivatives of the compounds of the invention, for instance those which have an acidic group or a sufficiently basic nitrogen. Particularly preferred are the pharmaceutically acceptable salts of the instant compounds which retain biological activity. Acid addition or cationic salts of the compounds of the invention are prepared in a standard manner.

Acid addition salts of the compounds of the present invention are prepared in a standard manner in suitable solvents.

In brief, an excess of an acid, such as hydrochloric, hydrobromic, sulfuric, phosphoric, acetic, maleic, or succinic, is added to the parent compound. In particular, the acetate salt form can be especially useful. In addition, certain of the compounds may form inner salts or zwitterions which may be acceptable. Cationic salts are prepared by treating the parent compound with an excess of an alkylating reagent, such as hydroxide,, carbonate or alkoxide containing the appropriate cation. Cations such as $Na^+$, $K^+$, $Ca^{2+}$ and $NH_4^+$ are examples of cations present in pharmaceutically acceptable salts.

The invention also includes the 3,4-dihydropyranchromenones of the compounds shown in the formula alone. These are prepared by known reduction methods.

Further, the invention includes the esters of compounds of the invention, especially lower alkyl esters, especially at the C-10 position.

Moreover, the invention includes the optically active amino analogues of compounds of the invention, especially substituted in the C-10 position of the molecule, wherein $R^3$ is $NH_2$, NHR or $NR_2$, with R being preferably lower alkyl.

When any variable (e.g., aryl, heterocycle, $R^1$, $R^2$, $R^3$, etc.) occurs more than one time in any constituent or in the compounds shown in the formula, its definition on each occurrence is independent of its definition at every other occurrence. Also, combinations of substituents and/or variables are permissible only if such combinations result in stable compounds. In accordance with the invention it is generally preferred that the $R^2$ substituent be a hydrophobic moiety, or more hydrophobic than substituent $R^1$.

The present invention further encompasses derivatives of compounds of the present invention comprising chemical modifications known to those skilled in the art. Chemical modifications include, but are not limited to, hydrolysis, esterification, acetylation, dehydration and alkylation, which do not destroy the inhibitory function(s) or the biological activity of the compounds of the present invention. Furthermore, several of the modifications may retain the ability to inhibit HIV infectivity at substantially the same or lower concentration than that of the unmodified compounds, but with reduced cytotoxicity.

In addition, as the compounds of the invention contain at least three chiral centers, all forms of such isomer(s) (i.e., stereoisomers) are considered to be an aspect of the invention (e.g., racemic mixtures, enantiomers, diastereomers, etc.).

Typical compounds of the invention have substituents as shown Table I.

TABLE I

| Compound | $R^1$ | $R^2$ | $R^3$ |
|---|---|---|---|
| 7a | isopropyl | 1-propyl | OH |
| -7a | isopropyl | 1-propyl | OH |
| 8a | isopropyl | 1-propyl | OH |
| -8a | isopropyl | 1-propyl | OH |
| 8b | methyl | 1-propyl | OH |
| 8c[b] | sec-butyl | 1-propyl | OH |
| 8d[b] | allyl | 1-propyl | OH |
| 8e[b] | propargyl | 1-propyl | OH |
| 13 | isobutyl | 1-methylpropyl | OH |
| -13 | isobutyl | 1-methylpropyl | OH |
| 14 | t-butyl | 2-methylpropyl | OH |
| -14 | t-butyl | 2-methylpropyl | OH |
| 15 | cyclohexyl | methyl | OH |
| -15 | cyclohexyl | methyl | OH |
| 16 | 1-cyclopentyl | methyl | keto |
| -16 | 1-cyclopentyl | methyl | keto |
| 17 | phenyl | 1-methylpropyl | $NH_2$ |
| -17 | phenyl | 1-methylpropyl | $NH_2$ |
| 18 | methylphenyl | ethyl | OH |
| -18 | methylphenyl | ethyl | OH |
| 19 | benzyl | methyl | OH |
| -19 | benzyl | methyl | OH |
| 20 | isopropyl | sec-butyl | $N_3$ |
| -20 | isopropyl | sec-butyl | $N_3$ |
| 21 | isopropyl | pentyl | $COOCH_3$ |
| -21 | isopropyl | pentyl | $COOCH_3$ |
| 22 | isopropyl | isobutyl | keto |
| -22 | isopropyl | isobutyl | keto |
| 23 | isopropyl | phenyl | OH |
| -23 | isopropyl | phenyl | OH |
| 24c | isopropyl | 1-propyl | OH |
| -24c | isopropyl | 1-propyl | OH |

[a]The designations (−)-7a and (−)-8a refer to the products in the "(−)" series that result from using (−)-(E)-crotyldiisopinocompheylborane in the reactions shown below with 3(a–e) in Schemes 1–3.
[b]Racemic mixtures are obtained using a crotyl-substituted organometallic reagent (type M-crotyl) bearing a ligand which is not optically active, like cyclohexyl or 2-methylcyclohexyl. The racemic mixtures are resolved by known procedures.
[c]3,4-dihydro compound.

$R^1$ and $R^2$ and $R^3$ are independently selected. $R^2$ and $R^3$ can also be a substituent described in the prior art with respect to calanolides, inophyllums and other coumarin derivatives as in PCT/US93/12500-WO 94/14789 and PCT/US94/05658-WO 94/28000.

DESCRIPTION OF THE BEST MODE OF SYNTHESIS

Figure 1:
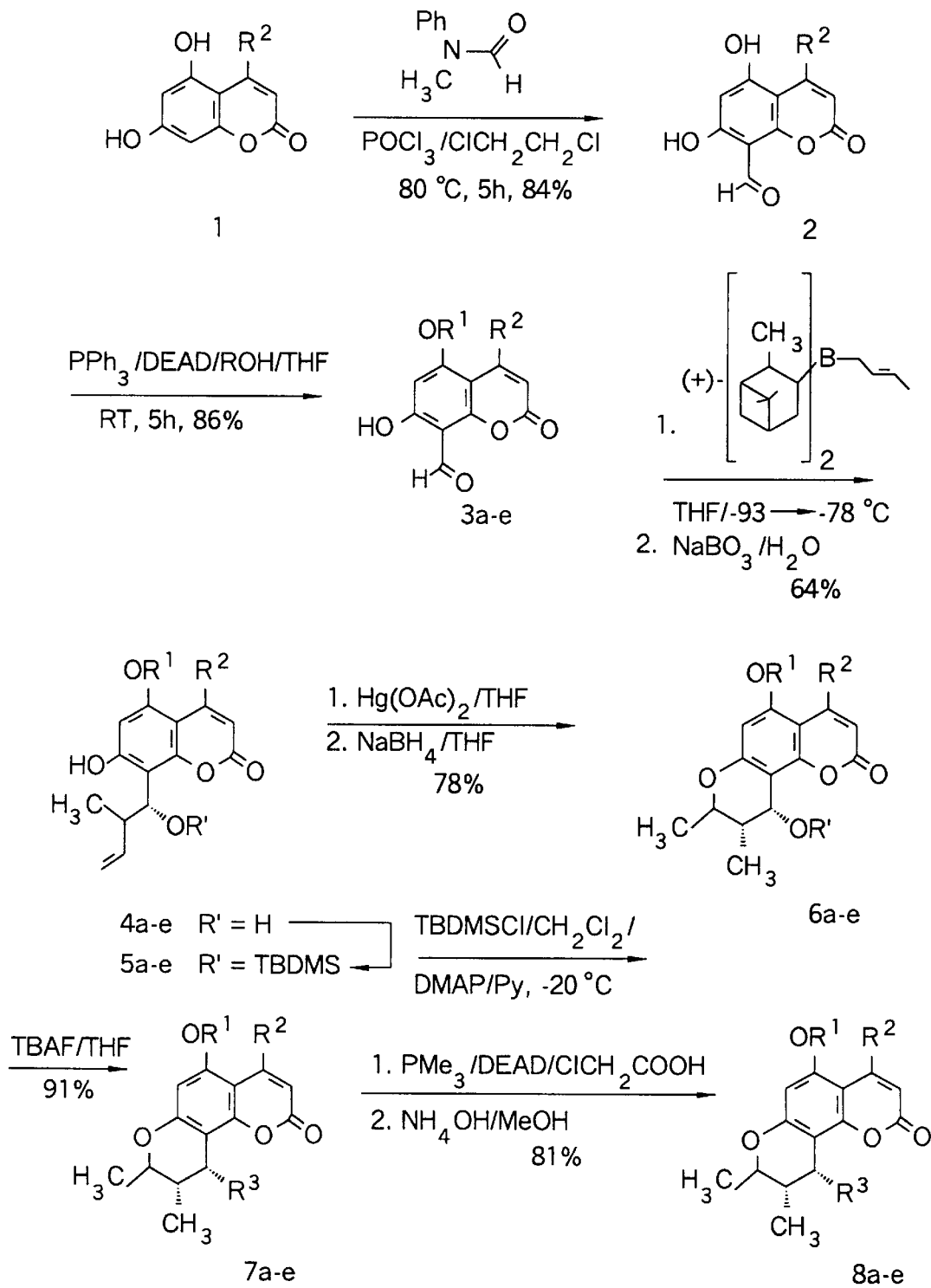
FIG. 1 illustrates Scheme 1 of the synthesis of the (+)-compounds and of the (−)- compounds of the invention.

In the development of the invention, various synthetic routes were explored without achieving the desired result. In accordance with the invention, several different successful schemes were developed, which are described hereinafter.

In accordance with Scheme 1 of the invention*, the known coumarin lactone 1, which is prepared from phloroglucinol as described by Chenera et al.,[6] is formulated at C-8 with N-methylformanilide in the presence of $POCl_3$ in 1,2-dichloroethane at 70°–75° C. to give aldehyde 2 in yields of 84% with a melting point of 236°–237° C. The site of the formylation was determined by NOE experiments.

*The Schemes 1–3 discussed below the letters "a", "b", "c", "d" and "e" designate substituents shown in Table 2, below.

Selective alkylation of the C-5 OH group is achieved using one of the selected alcohols under Mitsunobu conditions, i.e., according to the general procedure described by Mitsunobu[7] whereby an intermolecular dehydration occurs between alcohols and acid components on treatment such as with diethyl azodicarboxylate (DEAD) and triphenylphosphine ($Ph_3P$) under mild neutral conditions. In the present synthesis, a mixture of the selected alcohol, diethyl azodicarboxylate (DEAD), and triphenylphosphine ($Ph_3P$), are caused to react with coumarin 2 in a solution of tetrahydrofuran (THF). Thus, a solution of 2 in dry THF is treated with $Ph_3P$, DEAD, and 2-propanol. After reaction overnight, the 5-propyloxy derivative 3a is isolated as a white crystalline solid, mp 123°–125° C., in 86% yield. The compound was fully characterized by NMR spectroscopy and by elemental analysis.

This 5-(2-propyloxy) and other $R^1$-substituted derivatives are new compounds which are useful as described below.

The step of the synthesis is repeated with methyl, sec-butyl, allyl and propargyl alcohols to give the corresponding C-5 substituted derivative.

By this step of the synthesis, any of the desired substituents on the 5-carbon on the ring can be readily introduced.

Installation of the C-10 OH and the C-9 Me functional groups (which correspond respectively to the C-12 and C-11 positions in the natural calanolides) as sterogenically defined entities is achieved using the general procedure of Brown and Bhat.[8] (+)-(E)-Crotyldiisopinocampheylborane[8] was prepared in situ and reacted with compound 3a and borontrifluoride etherate at −93° C., then at −78° C., to give upon oxidative workup with sodium perborate, a 64% yield of (+)-7-hydroxy-8-[(1R,2R)-1-hydroxy-2-methylbut-3-enyl]-5-isopropyloxy-4-chromen-2-one (4a), a homo-allylic alcohol which is a new substance.

The purified syrupy product showed an $[\alpha]_D^{20}$+157° (c 2.6, chloroform). The compound was fully characterized by NMR spectroscopy and by elemental analysis.

The homoallylic alcohol adduct 4a was O-protected by converting to the tert-butyldimethylsilyl derivative 5a under the agency of tert-butylchlorodimethylsilane, imidazole, and 4-dimethylaminopyridine in dichloromethane at 0° C. The protected derivative was obtained in 88% yield after purification by silica gel chromatography. The syrupy product showed an $[\alpha]_D^{20}$+38.0° (c 1.1, $CHCl_3$). This monosilylated compound is a new substance. The compound was sully characterized by NMR spectroscopy and by elemental analysis.

Only monosilylated 5a was obtained as a product. It is probable that the phenolic OH group of 4a is too sterically hindered to react with a bulky $t$-$BuMe_2Si$ function.

Ring-closure to the fused pyran-chromenone compound 6a was achieved using a mercuric acetate-mediated cyclization as follows: A solution of 5a in THF was treated with $Hg(OAc)_2$, followed by reduction of the organomercury intermediate with $NaBH_4$. Silica gel purification of the crude product afforded the cyclized product 6a in 78% yield as a syrup that showed an $[\alpha]_D^{20}$−35° (c 1.1, $CHCl_3$). The product was fully characterized by NMR spectroscopy and by elemental analysis. This fused pyran-chromenone is a new substance.

Removal of the silyl ether protecting group of 6a was achieved using tetrabutylammonium fluoride in THF at room temperature. Column chromatography of the crude product afforded 7a in 91% yield as a syrup that showed $[\alpha]_D^{20}$+26.5° (c 1.1, $CHCl_3$). NMR spin-spin coupling data confirmed that the compound thus obtained has a trans, cis relative stereochemistry at C-8—C-9—C-10 and thus is of the 8R, 9S, 10R stereochemistry that is analogous to that of (+)-calanolide B. The product (+)-7a, which is a new substance, was fully characterized by NMR spectroscopy and by elemental analysis. The compound may be used to lower the potency of compounds of the invention which are highly potent, like compound (−)-7a, in situations where this is desired. Compound (+)-7a is uniquely useful to generate its 10-epimer, (+)-8.

In a like manner compounds (−)-7b-e are synthesized. They too are uniquely useful to generate their respective 10-epimer.

Epimerization of the C-10 hydroxy functional group of (+)-7a to give the 8R, 9S, 10S stereochemistry of (+)-8a, which is analogous to that of the known (+)-calanolide A, was carried out using a modified Mitsunobu reaction as follows: A solution of (+)-7a in THF maintained at −78° C. was treated with diethyl azodicarboxylate, trimethylphosphine, and chloroacetic acid. Upon reaction at low temperatures (−78° to −30° C.), followed by a hydrolytic workup in aqueous ammonia, the pure epimerized product (+)-8a was obtained in 81% yield as a syrup that had $[\alpha]_D^{20}$+106° (c 1.1, $CHCl_3$). The relative stereochemistry, trans, trans at C-8, C-9 and C-10, was confirmed by NMR coupling constants. The absolute stereochemistry for (+)-8a is thus confirmed as 8R, 9S, 10S, analogous to that of the known (+)-calanolide A. The compound was fully characterized by NMR spectroscopy and by elemental analysis. The compound is new.

Analysis of both products (+)-7a and (+)-8a [and their enantiomers, generated below] by chiral-phase chromatography on a column of D-phenylglycine polymer (Regis Reversible D-phenylglycine) with 90:10 hexanes-2-propanol as eluent and UV detection showed the compounds to be ≧95% in optical purity, optionally ≧99%.

Whenever in the description reference is made to "alkylation", this terminology is intended to include the introduction of an $R^1$ substituent at the 5-carbon on the chromenone ring.

When the substituent on the coumarin lactone 1 is other than an alkyl, as shown by $R^2$, an appropriate reaction sequence to prepare the modified lactone is that shown by Chenera et al.[6]. For instance phloroglucinol is reacted with $R^2C(=O)CH_2C(=O)OEt$ with $CF_3SO_3H$ carried at about or at room temperature. Where $R^2$ is methyl, the reactant is $MeC(=O)CH_2C(=O)OEt$.

Other Embodiments of the Reaction Sequence

By carrying out the sequence beginning with 2 and substituting other alcohols ($R^1OH$) in the reaction to give 3, the C-5 $R^1$-group can be modified as desired. For instance, MeOH gives the Me- compound 3b; sec-BuOH gives the sec-Bu- compound 3c, allyl alcohol gives the $CH_2=CHCH_2$— compound 3d, and propargylic alcohol gives the $HC≡CCH_2$— compound 3e. Cyclohexyl alcohol and benzyl alcohol, yield the correspondingly substituted compounds. The compounds of the invention which have other substituents in $R^1$ or $R^2$ are made in a similar manner.

By using with a coumarin lactone wherein the $R^2$ substituent is other than alkyl, the corresponding compounds of the invention are obtained as described herein where $R^2$ has the designation described herein above.

By chemistry wholly analogous to that described above for the (+)- series depicted in Scheme 1, compounds 3b, 3c, 3d, and 3e are carried through the sequence to give each intermediate and final products 7b, 7c, 7d, and 7e, of the (−)-series and 8b, 8c, 8d, and 8e of the (−)-compound series.

TABLE 2

Physicochemical data for compounds of type 7 and 8.[a]

| Compound | $R^1$ | $[\alpha]^{80}$ | mp (°C.) | Molecular Formula | Elemental Analysis |
|---|---|---|---|---|---|
| 7a | isopropyl | +22.9° (c 1.1, CHCl$_3$) | syrup | $C_{20}H_{26}O_5$ | Calcd. C: 69.34, H: 7.56 Found C: 69.15, H: 7.93 |
| -7a | isopropyl | -28° (c 1.1, CHCl$_3$) | foam | $C_{20}H_{26}O_5$ | Calcd. C: 69.34, H: 7.56 Found C: 69.10, H: 7.49 |
| 7b[b] | methyl | | 94–96 | $C_{18}H_{22}O_5$ | Calcd. C: 67.91, H: 6.96 Found C: 67.95, H: 7.02 |
| 8a | isopropyl | +106° (c 1.1, CHCl$_3$) | syrup | $C_{20}H_{26}O_5$ 0.03 CH$_2$Cl$_2$ | Calcd. C: 65.50, H: 7.21 Found C: 65.74, H: 7.39 |
| -8a | isopropyl | -90.7° (c 1.1, CHCl$_3$) | syrup | $C_{20}H_{26}O_5$ | Calcd. C: 69.34, H: 7.56 Found C: 69.43, H: 7.39 |
| 8b[b] | methyl | | 134–136 | $C_{18}H_{22}O_5$ | Calcd. C: 69.71, H: 6.96 Found C: 67.71, H: 7.04 |
| 8c[b] | sec-butyl | | syrup | $C_{21}H_{28}O_5$ 0.35 H$_2$O | Calcd. C: 68.77, H: 7.89 Found C: 68.75, H: 7.90 |
| 8d[b] | allyl | | 98–100 | $C_{20}H_{23}O_5$ | Calcd. C: 67.89, H: 6.88 Found C: 67.89, H: 7.11 |
| 8e[b] | propargyl | | 88–98 | $C_{20}H_{22}O_5$ 0.88 H$_2$O | Calcd. C: 67.06, H: 6.68 Found C: 67.06, H: 6.69 |

[a]The designations (–)-7a and (–)-8a refer to the products in the "(–)"series that arise from using (–)-(E) crotyldiisopinocampheylborane in the reaction with 3a.
[b]Racemic compound.

By repeating the entire process, beginning with compound 3a and using the enantiomeric form of the organoborane reagent, (–)-(E)-crotyldiisopinocampheylborane,[8] the enantiomeric series of compounds are made yielding the (–)-7 compounds and the (–)-8 compounds. If anti-HIV activity is considered the most important criteria, the most important compound in this series is the epimer (–) of the calanolide B series, herein designated as (–)-7a, wherein for the present $R^1$ is preferably isopropyl and $R^2$ is propyl. In the A series, the most important epimer is the (+)-8 epimer in which $R^1$ and $R^2$ have the same meaning as noted above.

The (–)-8 compound may be used to lower the potency of the compounds of the invention that are highly potent, for instance in the NCI primary anti-HIV assay.

Physicochemical data for compounds 7a–b and 8a–e are provided in Table 2.

Alternative Synthesis Embodiments

The synthesis of the compounds of the invention lends itself to alternatives in the selection or reagents and/or conditions for the chemical processes, which are readily available for one skilled in the art. These are described herein below.

To synthesize the formylated lactone 2 from the coumarin lactone 1, there may be used, in general, the Vilsmeier-Haack reaction whereby an activated aromatic or heterocyclic compound is reacted with disubstituted formadines and phosphorous oxychloride. For instance, there may be reacted other formamides like N-methylformanilide or other N,N-dialkyl-, N,N-arylaklyl-, or N,N-diarylformamides, especially N,N-dimethylformamide, in the presence of POCl$_3$ or other related chalcogen-metal halides, or phosgene (COCl$_2$), in 1,2-dichloroethane or other nonpolar aprotic solvent, including chlorinated hydrocarbons. "Alkyl" is generally a short-chain alkyl group of to 4 carbon atoms, preferably methyl. "Aryl" is generally phenyl or lower alkyl-substituted phenyl group.

The temperature of the reaction is preferably in the range of 40°–100° C., preferably in 1,2-dichloroethane at about 75° C. under conditions or a typical Vilsmeier reaction.[9] Other methods of aromatic ring formulation, e.g., the Gatterman-Koch reaction[10] or the Gatterman aldehyde reaction[11] or improved versions thereof, may be used.

For introducing the selected substituent $R^1$, e.g., alkylation of the C-5 OH functional group to give compounds of type 3, as described above, any method of phenolic hydroxyl group alkylation may be used. Thus a great number of primary and secondary alkyl-, arylalkyl-, and cycloalkyl halides, sulfates, sulfonates, especially alkyl and substituted-alkyl sulfonates, including the trifluoromethanesulfonate, and aryl and substituted-aryl sulfonates, including the p-toluenesulfonate, and the like, may be caused to react with a metallic salt of compound 2 (e.g., the sodium or potassium salt) under conditions of general ether formation (e.g., the typical Williamson ether synthesis[12]) to give variations of 3. Preferred organic solvents include, but are not limited to, ethereal solvents, including THF, dioxane and the like, and polar aprotic solvents such as N,N-dimethylformamide, dimethyl sulfoxide, hexamethylphosphoric triamide, and the like. The preferred method is that described in the foregoing section using embodiments of the Mitsunobu reaction.[7] Where the substituents are other than "alkyl" on the 5-carbon on the chromenone ring, the selected substitutions are readily introduced by known reactions.

In order to synthesize the enantiomerically pure β-homoallylic alcohol of type 4, there may be used any appropriate optically active organoborane reagent such as the crotyl-substituted organometallic reagent. (type M-crotyl) bearing a suitable optically active ligand, where M=B, Sn, Al, Si, Ti or other metal or metalloid. The optically active ligands may be of any suitable asymmetric organic moiety that might include, but is not restricted to, the following: monoisocampheylborane,[13] limonylborane,[14] 2- and 4-dicaranyl-boranes,[15] myrtanylborane,[16] or dilongifolylborane[17] as disclosed in the respective references identified below, which are incorporated herein by reference.

It is to be noted that the enantiomeric series leading to the (+)- and (–)-series of enantiomers of structure types 7 and 8, as well as their enantiomeric purity thereof, is influenced by the choice of an optically active ligand, which can readily be made by one skilled in the art from knowledge in the art. By appropriate selection from the optically active ligands disclosed herein and others available in the chemical literature, one skilled in the art will readily select the appropriate ligand to yield the desired end product.

The temperature of the reaction may vary between about −20° and −100° C., with the range of −93° up to −78° C. being preferred; however, chemical reactivity may become unacceptably low at lower temperatures. It is noted that lower temperatures in general tend to give higher enantiomeric purities; hence, these are generally preferred. Times may vary from 0.1 h to 24 hours; a period of 0.5 hours at −93° C., followed by stirring at −78° C. is preferred. Oxidative workup of the organoborane reaction may be carried out with $H_2O_2$ and alkali metal or alkaline earth metal base, but sodium perborate[18] is the preferred reagent.

The order of reaction can be readily altered for the production of compounds of type 4. Thus, the (E)-crotyldiisopinocampheylborane reagent can be caused to react directly with compound 2, and the alkylation of the 5-OH functional group can be delayed to a later step, i.e., steps two and three in Scheme 1 could be reversed.

Alternative reagents for the silylation of compounds of type 4 include, but are not limited to, the following: $Me_3SiX$, $t$-$BuPh_2SiX$, or other trialkyl, mixed aryl-alkyl- or triarylsilyl halides with suitable base in a dry, aprotic solvent. X may be halogen, such as chlorine or bromine, or other suitable leaving group, including, but not limited to, sulfonic acid ester, perchlorate ester, and the like. The TBDMSCl ($t$-$BuMe_2SiCl$) reagent is, however, preferred. Reaction temperatures may range from −50 to +50° C.; however, −10° to −30° C. might be satisfactory, about −20° C. being preferred.

While bulky silicon-based protecting groups are preferred for the 1'-OH group of compounds of type 5, any alkyl, aryl, or acyl derivative. capable of forming a suitable protective ether or ester derivative for the 1'-OH group may be used.

Alternatives to the mercury-assisted cyclization of the orthoalkenylphenol of type 5 to give compounds to type 6 include any electrophilic process known to ring-close acyclic alkenes with phenolic compounds to form O-heterocycles. Reagents include, but are not limited to, Lewis acids of various types, e.g., halogens, especially iodine; N-haloimides, especially N-bromosuccinimide; alkyl- and arylselenium halides of the type RSeX; and sulfur halide reagents of the type RSX. Such processes are generally known to those familiar with the art.

In accordance with Scheme 2 which shows an alternative to the aforedescribed process, homoallylic compounds of type 9, which are related structurally to those of type 5, can be prepared by reaction of the appropriate chiral allyl borane reagent with 3a–e. The process is wholly analogous to the production of compounds of type 5. The protected intermediates of type 9 are then ring closed with any of the above-mentioned procedures, but especially effective is the mercuric acetate-sodium borohydride procedure. Deprotection of the 10-OH function with tetrabutylammonium fluoride or related reagent, followed by oxidation, gives the ketone of type 10. Oxidants include pyridinium chlorochromate, pyridinium dichromate, or other chromium-based reagent, or a suitable catalyst and oxygen, or a dimethyl sulfoxide-based reagent. Subsequent α-alkylation with MeI, $(MeO)_2SO_2$, or related reagent in suitable base, lithium hexamethyldisilazide being preferred as in the example described by Rama Rao and co-workers,[19] gives the resultant trans-9,10-dimethylpyranone of type 11. Reduction of the pyranone intermediate with $NaBH_4$ as described above, or with the Luche reagent,[5] or with a related alkali or alkaline earth metal borohydride or other selective metal hydride reducing agent, gives the 10-OH compounds of type 7 (or 8). Especially selective in this regard are a number of oxidoreductases, either crude, purified, or immobilized on solid support, that are available from yeast or other microbial sources that are known to selectively reduce such ketones.[20]

Upon epimerizing the respective compound, the corresponding epimer is obtained, as described above.

The process shown in Scheme 2 is also amenable to producing the (−)- set of enantiomers by changing the organoborane reagent, from one of (+)-optical rotation to one of (−)-optical rotation, as described above.

Scheme 3 shows an alternative ring closure effected on an acyclic keto compound such as that of type 12. Compounds of type 12 may be directly obtained by reaction of tigloyl chloride with 1 as taught by Chenera et al.[6] Ring closure of 12a–e may be effected by any of the procedures described for the conversion of compounds of type 5 to those of type 6. In addition, simple heating of type 12 ketones is sufficient to effect ring closure, predominantly to the trans species. Alternatively, a recent publication[21] indicates that a cesium fluoride-induced intramolecular Michael reaction gives high diastereoselectivity upon ring closure for compounds of similar structure to that of type 12. Reduction of the cyclized keto intermediate with any mild, selective reagents, including, but not limited to, sodium borohydride or other alkali metal or quaternary ammonium borohydrides, or related species gives compounds of type 7 or 8 (or mixtures thereof). Luche-type reductions[22] are stated to favor the products having the 10-OH group on the β-face of the molecule, i. e., compounds of type 8. Exceptionally mild and selective reagents include the oxidoreductases from various yeasts and bacterial sources that are capable of reducing such ketones to secondary alcohols of specific stereochemistry with high stereoselectivities.[20]

Desilylation of the intermediate compounds of type 6 (Scheme 1) or type 9 (Scheme 2) may be performed by other reagents including any tetraalkyl-, tetraaryl-, or mixed aryl-alkylammonium fluoride, pyridinium fluoride, HF-acetonitrile, or solutions of HF salts in aprotic media, or the common mineral acids in aprotic or protic media.

In general, to convert epimers of type (+)-7 to their (+)-series A analogues, which are compounds of type (+)-8, a modification of the Mitsunobu reaction[7] was utilized, whereby chloroacetic acid instead of the usual $RCO_2H$ reagents, where R=alkyl or aryl, was used. The α-chloroacetate intermediate is exceptionally facile of cleavage under mildly basic conditions. Acidic ArOH compounds may also be used for the ester hydrolysis. A further modification of the Mitsunobu reaction is to use $Me_3P$ instead of the usual $Ph_3P$ reagent.[3,4] Advantages of $Me_3P$ over the latter apparently lie in its small steric bulk that facilitates reaction with the 10-OH compound, and the fact that the unreacted compound is volatile and easily removed during workup of the reaction mixture. Alternatives to $Me_3P$ include any trialkyl-, triaryl- or mixed alkyl-arylphosphine reagent as taught in the seminal work of Mitsunobu.[7] Alternatives to diethylazodlcarboxylate include any dialkyl-, diaryl-, or mixed alkyl-aryl azodicarboxylate reagent. Temperatures may range from −100° C. to 50° C., although the range of −78° C. to −30° C. is the preferred range.

Saponification of the resulting carboxylic acid ester intermediate from the Mitsunobu reaction can be effected with ammonium hydroxide-methanol mixtures at −30° C. to +40° C., although a range of −30° C. to 0° C. is preferred Any trialkyl-, triaryl- or mixed alkyl-aryl ammonium base or other alkali or alkaline earth metal hydroxide may be used, although NH$_4$OH in acetonitrile or other aprotic solvent can be used.

To prepare the (−)-B epimers, designated as (−)-7 and (−)-8 in Scheme 1, the alternative embodiments of Schemes 2 and 3 may be used.

Whenever a temperature range is provided, it will be understood that operating outside the range is likely to give less-than-optimum results.

Figure 2:
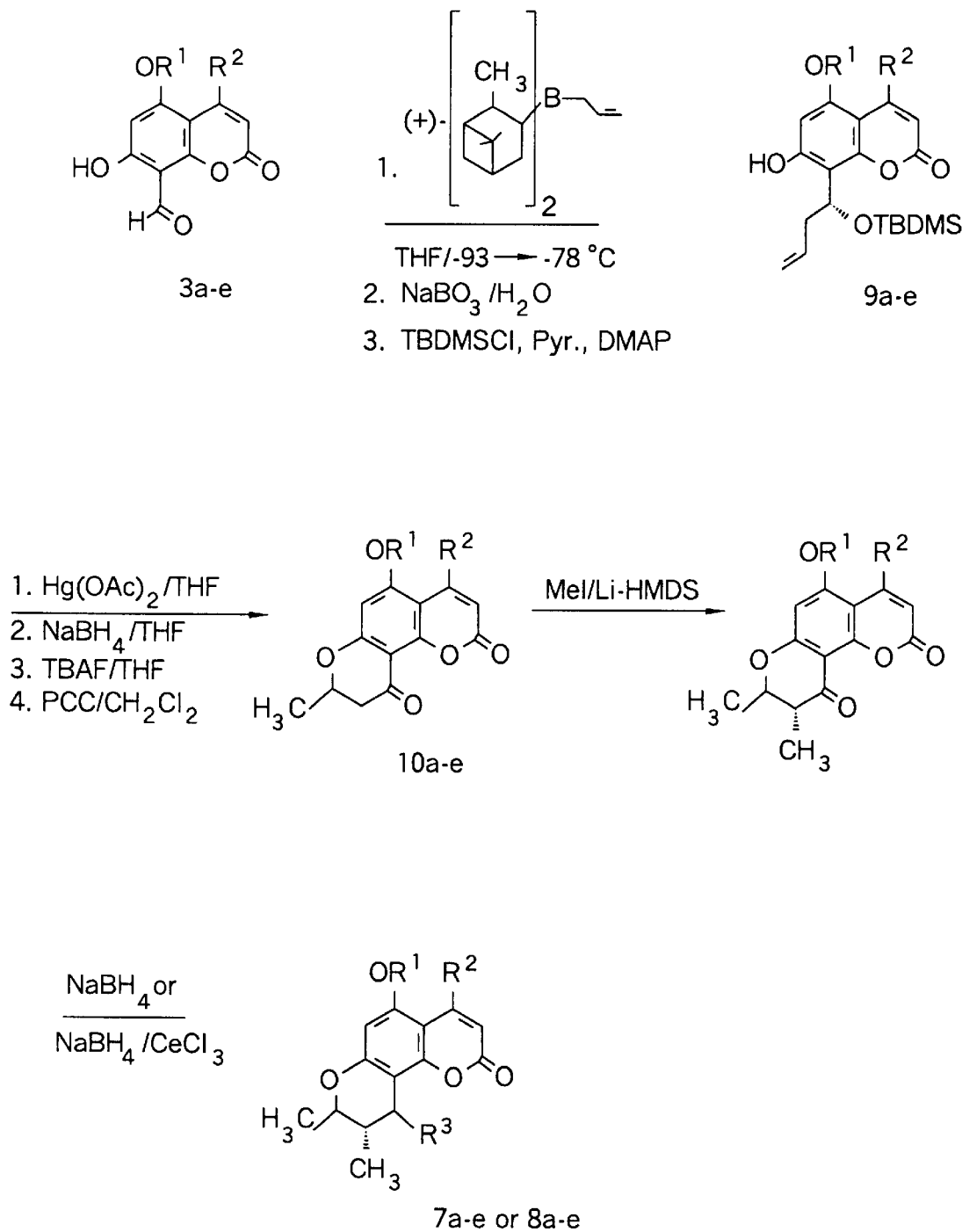
FIG. 2 illustrates Scheme 2 of the synthesis of compounds of the invention.
Figure 3:
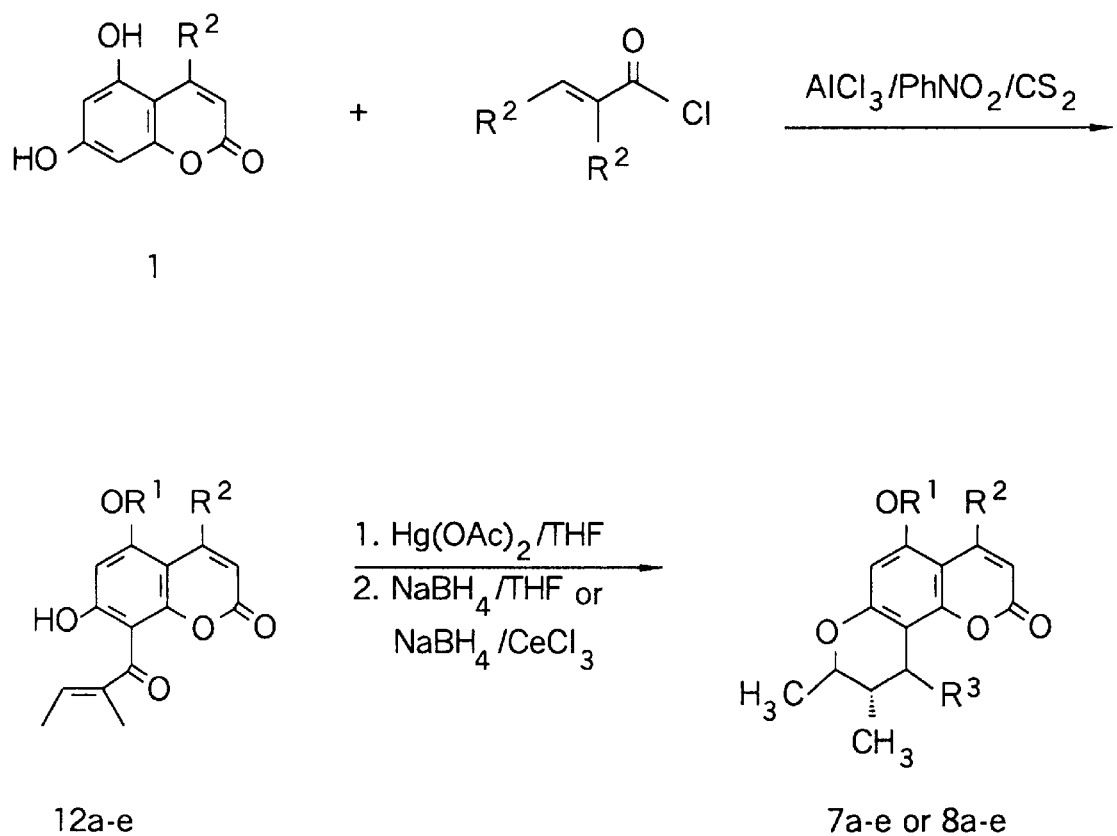
FIG. 3 illustrates Scheme 3 of the synthesis of compounds of the invention.

In the reaction Schemes 1–3 shown in FIGS. 1–3, the compounds listed in Table 1 are prepared by the reactions shown herein and the products are identified by the numerals given in the Table, and the intermediates correspond to those shown in the reactions shown in the Figures but for the substituents on the intermediates and the final products, which are as shown in Table 1.

The following nonlimiting examples are provided for illustrative purposes.

EXAMPLES

General Methods.

All reactions were monitored by thin-layer chromatography (TLC). Adsorption chromatography was carried out using E. Merck silica gel products: (a) TLC on 0.2-mm aluminum-backed plates, (b) column chromatography using 230–400 mesh silica gel. Visualization of the TLC plates was by 254-nm UV light and by spray-heat development using a p-anisaldehyde-sulfuric acid reagent.[23] The solvent system for column chromatography was A, 9:1 hexane-ethyl acetate; B, 8:2 hexane-ethyl acetate. Anhydrous solvents were prepared as follows: dichloromethane, pyridine and triethylamine were distilled from calcium hydride. Diethyl ether was distilled from lithium aluminum hydride. Tetrahydrofuran (THF) was refluxed with sodium-benzophenone ketyl and distilled. N,N-Dimethylformamide was distilled over calcium hydride under reduced pressure. All reactions were carried out under a nitrogen atmosphere unless otherwise indicated. Solvents were evaporated at aspirator vacuum at about 40° C., unless otherwise indicated. Melting points were determined using a Thomas-Hoover "Unimelt" capillary melting point apparatus equipped with a Cole-Parmer model 8520-50 Digi-Sense digital thermocouple combination that was calibrated with known standards. Elemental analyses were furnished by Atlantic Microlab, Inc. of Atlanta, Ga. $^1$H and $^{13}$C NMR spectra were determined at 250 MHZ and 62.5 Hz respectively as ca. 0.1% solutions in CDCl$_3$ using a Bruker AM 250 instrument. $^1$H NMR chemical shifts are reported as δ (ppm) downfield from an internal standard of tetramethylsilane (TMS); multiplicities are first-order values in Hz: s, singlet; d, doublet; t, triplet; dd, doublet of doublets; m, multiplet. The exchangeable protons of hydroxy groups were determined by deuterium exchange using deuterium oxide. $^{13}$C NMR chemical shifts are reported as δ (ppm) relative to CDCl$_3$ (77.00 ppm) as standard. Optical rotations were measured with a Perkin-Elmer Model 243 automatic polarimeter for solutions in a 0.1-dm cell at the indicated temperature. The mass spectral analysis was obtained on a VG-ZAB instrument at the University of Tennessee.

7-Hydroxy-5-isopropyloxy-2-oxo-4-propyl-2H-8-carbaldehyde (3a).

To a solution of 2[4] (5 g, 20.15 mmol) in dry THF (100 mL) was added PPh$_3$ (5.80 g, 20.2 mmol), diethyl azodicarboxylate (DEAD, 0.35 mL, 20.2 mmol) dropwise, and 2-propanol (1.55 mL, 20.2 mmol), and the mixture was stirred under nitrogen for 5 h. Then water (20 mL) was added. The mixture was extracted with EtOAc (3×50 mL). All organic layers were combined, dried (MgSO$_4$), concentrated, and submitted for column chromatography (solvent A) to obtain 5.0 g (86%) of 3 as a white solid: mp 123°–125° C.; $^1$H NMR (CDCl$_3$): δ1.02 (t, 3 H, J=7.3 Hz, —CH$_2$CH$_2$CH$_3$), 1.46 [d, 6 H, J=6.0 Hz, —CH(CH$_3$)$_2$], 1.64 (m, 2 H, —CH$_2$CH$_2$CH$_3$), 2.87 (t, 2 H, J=7.4 Hz, —CH$_2$CH$_2$CH$_3$), 4.7 6 [m, 1 H, —CH(CH$_3$)$_2$], 6.02 (s, 1 H, H-3), 6.26 (s, 1 H, H-6), 10.39 (s, 1 H, —CHO), 12.65 (s, 1 H, —OH); $^{13}$C NMR (CDCl$_3$): δ 13.77, 21.60 (2C), 23.02, 38.85, 72.41, 96.39, 103.44, 103.99, 111.27, 158.27, 159.08, 162.87, 166.78, 191.93. Anal. Calcd for C$_{16}$H$_{18}$O$_5$: C, 66.20, H, 6.25. Found: C, 66.12, H, 6.22.

(+)-7-Hydroxy-8-[(1R,2R)-1-hydroxy-2-methylbut-3-enyl]-5-isopropyloxy-4-propyl-chromen-2-one (4a).

(+)-(E)-Crotyldiisopinocampheylborane was prepared in situ according to the procedure of Brown and Bhat.[8] To a stirred mixture t-BuOK (2.31 g, 20.7 mmol), THF (15 mL), and trans-butene (4.0 mL, 44 mmol) was added BuLi (8.26 mL, 20.7 mmol, 2.5M in hexane). The mixture was then kept at −50° C. for 10 min and, then cooled to −93° C., at which time (+)-β-methoxydiisopinocampheylborane (6.52 g, 20.68 mmol) in THF (10 mL) was added dropwise over a period of 20 min. The reaction mixture was stirred at −93° C. for 30 min, and borontrifluoride etherate (2.53 mL, 20.7 mmol) was then added dropwise over a period of 5 min, followed by compound 2 (3.00 g, 10.3 mmol) in THF (15 mL) over a period of 10 min. The mixture was stirred at −93° C. for 30 min, then at −78° C. for 5 h. After this time, sodium perborate[18] (6.34 g, 41.20 mmol) and water (15 mL) were added, and the mixture was stirred, gradually warming up to room temperature. The mixture was stirred for 10 h. Brine (20 mL) was added, and the organic layer was separated. The aqueous layer was extracted with EtOAc (2×25 mL), and the combined organic layers were dried (MgSO$_4$), concentrated, and submitted to silica gel chromatography (solvent B) to obtain 4a (2.35 g, 64%) as a syrup: $[\alpha]_D^{20}$+ 157° (C 2.6, CHCl$_3$); $^1$H NMR (CDCl$_3$): δ 0.99 (t, 3 H, J=7.3 Hz, —CH$_2$CH$_2$CH$_3$), 1.06 (d, 3 H, J=6.9 Hz, —CHCH$_3$), 1.39 and 1.41 [2d, 6 H, J=5.9 Hz, —CH(CH$_3$)$_2$], 1.58 (m, 2 H, J=7.65 Hz, —CH$_2$CH$_2$CH$_3$), 2.65 (q, 1 H, J=7.29 Hz, —CHCH$_3$), 2.83 (bt, 2 H, J=7.5 Hz, —CH$_2$CH$_2$CH$_3$), 4.23 (bs, 1 H, —CHOH), 4.62 [m, 1 H, —CH(CH$_3$)$_2$], 5.08–5.15 (m, 2 H, —CH═CH$_2$), 5.37 (d, 1 H, J=6.9 Hz, —CHOH), 5.81 (s, 1 H, H-3), 5.86–5.97 (m, 1 H, —CH═CH$_2$), 6.27 (s, 1 H, H-6), 9.57 (s, 1 H, Ar—OH): $^{13}$C NMR (CDCl$_3$): δ 13.91, 16.46, 21.77 (2C), 23.12, 38.96, 44.65, 70.68, 72.64, 98.02, 103.52, 105.76, 109.46, 117.04, 139.73, 153.37, 156.15, 159.56, 160.58, 161.40. Anal. Calcd. for C$_{20}$H$_{26}$O$_5$: C, 69.34, H, 7.56. Found C, 69.24; H, 7.62.

(+)-7-Hydroxy-8-[(1R,2R)-1-tert-butyldimethylsilyloxy-2-methylbut-3-enyl]-5-isopropyloxy-4-propyl-chromen-2-one (5a).

To a solution of 4a (500 mg, 1.44 mmol) in dry CH$_2$Cl$_2$ (20 mL) at 0° C. was added DMAP (88 mg, 0.72 mmol), imidazole (196 mg, 2.88 mmol) and tert-butylchlorodimethylsilane (239 mg, 1.59 mmol). The reaction mixture was allowed to warm up to room temperature and stirred for 24 h. Water (10 mL) was then added, the organic layer was separated, dried (MgSO$_4$), concentrated and submitted to silica gel chromatography (Solvent B) to obtain 5a (583 mg, 88%) as a syrup: [α]$_D^{20}$+38.0° (c 1.1, CHCl$_3$); $^1$H NMR (CDCl$_3$): δ −0.04 (s, 3 H, —SiCH$_3$), 0.14 (s, 3 H, —SiCH$_3$), 0.87 [s, 9 H, —C(CH$_3$)$_3$], 0.97 (d, 3 H, J=6.88 Hz, —CHCH$_3$), 1.00 (t, 3 H, J=7.44 Hz, —CH$_2$CH$_2$CH$_3$), 1.38 and 1.40 (2d, 6 H, J=6.0 Hz, —CH (CH$_3$)$_2$), 1.62 (m, 2 H, —CH$_2$CH$_2$CH$_3$), 2.59 (q, 1 H, J=6.9 Hz, —CHCH$_3$), 2.86 (bt, 2 H, —CH$_2$CH$_2$CH$_3$), 4.62 [m, 1 H, J=6.06 Hz, —CH(CH$_3$)$_2$], 4.95–5.05 (m, 2 H, —CH=CH$_2$), 5.29 [d, 1 H, J=6.5 Hz, —CHOSi(CH$_3$)$_2$—], 5.85 (m, 1 H, —CH=CH$_2$), 5.89 (s, 1 H, H-3), 6.24 (s, 1 H, H-6), 9.15 (s, 1 H, ArOH); $^{13}$C NMR (CDCl$_3$): δ −0.33, −0.15, 13.91, 16.27, 18.06, 21.76, 21.85, 23.08, 25.68, 25.88, 38.96, 44.62, 70.67, 74.28, 97.54, 103.39, 106.57, 109.86, 115.71, 139.60, 152.98, 156.13, 158.95, 160.17, 160.75. Anal. Calcd for C$_{26}$H$_{40}$O$_5$Si: C, 67.78; H, 8.75. Found C, 67.91; H, 8.71.

(−)-(8R,9R,10R)-10-tert-Butyldimethylsilyloxy-5-isopropyloxy-8,9-dimethyl-4-propyl-9,10-dihydro-8H-pyrano[2,3-f]chromen-2-one (6a).

To a solution of 5a (500 mg, 1.09 mmol) in THF (20 mL) was added Hg(OAc)$_2$ (518 mg, 1.62 mmol), and the mixture was stirred for 45 min at room temperature, then cooled to 0° C. NaBH$_4$ (410 mg, 10.8 mmol) was added, and the reaction was allowed to warm to room temperature and stirred for an additional 45 min. The organic layer was separated, washed with brine (5 mL), dried (MgSO$_4$), concentrated, and submitted for silica gel chromatography (Solvent B) to give 6 (393 mg, 78%) as a syrup: [α]$_D^{20}$ −35° (c 1.1, CHCl$_3$); $^1$H NMR (CDCl$_3$): δ −0.17 (s, 3 H, —SiCH$_3$), 0.20 (s, 3 H, —SiCH$_3$), 0.74 [s, 9 H, —SiC(CH$_3$)$_3$], 0.92 (t, 3 H, J=7.30 Hz, —CH$_2$CH$_2$CH$_3$), 0.99 (d, 3 H, J=6.8 Hz, —CHCH$_3$), 1.28–1.38 [m, 9 H, —CH(CH$_3$)$_2$], —CHCH$_3$), 1.5–1.65 (m, 3 H, H-9, —CH$_2$CH$_2$CH$_3$), 2.83 (mm, 2 H, —CH$_2$CH$_2$CH$_3$), 4.32 (m, 1 H, J=4.5 Hz, H-8), 4.55 (m, 1 H, J=5.95 Hz, —CH(CH$_3$)$_2$), 4.93 (bd, 1 H, J=1.89 Hz, —CHOSi(CH$_3$)$_2$—), 5.84 (s, 1 H, H-3), 6.12 (s, 1 H, H-6); $^{13}$C NMR (CDCl$_3$): δ −4.79, −4.49, 13.85, 14.16, 18.53, 19.24, 21.77, 21.86, 23.12, 26.03, 38.92, 39.21, 62.61, 70.60, 70.91, 96.55, 103.54, 106.63, 110.02, 154.20, 156.29, 158.04, 158.83, 160.77. MS (positive-ion FAB): m/z 461 [M+1]$^+$, 417, 329.

It is noteworthy that, although 6 is an intermediate in the (+)-series, it showed a (−)-optical rotation.

When excess NaBH$_4$ was used, and reaction times were prolonged, considerable loss of the t-BuMe$_2$Si group was observed, directly giving 7a.

(+)-(8R,9S,10R)-10-Hydroxy-5-isopropyloxy-8,9-dimethyl-4-propyl-9,10-di-hydro-8H-pyrano[2,3-f]-chromen-2-one (7a).

To a solution of 6a (130 mg, 0.29 mmol) in THF (5 mL) was added Bu$_4$NF (1.45 mL, 1M solution in THF) at 0° C. The reaction mixture was stirred at room temperature for 6 h. Water was added (2 mL), followed by brine (2 mL). The solution was extracted with ether (3×5 mL). The combined organic layers were dried (MgSO$_4$), concentrated, and submitted for silica gel chromatography (Solvent B) to obtain 7a (92 mg, 91%) as a syrup: [α]$_D^{20}$+26.5° (c 1.1, CHCl$_3$); $^1$H NMR (CDCl$_3$): δ 0.97 (t, 3 H, J=7.3 Hz, —CH$_2$CH$_2$CH$_3$), 1.08 (d, 3 H, J=7.0 Hz, —CHCH$_3$), 1.37 [d, 9 H, J=6.2 Hz, —CH(CH$_3$)$_2$, CHCH$_3$], 1.57 (m, 2 H, —CH$_2$CH$_2$CH$_3$), 1.70 (m, 1 H, H-9), 2.99 (m, 2 H, —CH$_2$CH$_2$CH$_3$), 4.22 (m,1 H, H-8), 4.59 [m, 1 H, —CH (CH$_3$)$_2$], 4.91 (d, 1 H, J=2.7 Hz, H-10), 5.88 (s, 1 H, H-3), 6.16 (s, 1 H, H-6); $^{13}$C NMR (CDCl$_3$): δ 12.49, 13.84, 18.83, 21.69, 21.74, 23.15, 38.38, 38.89, 61.65, 70.65, 72.87, 96.65, 104.20, 106.18, 110.10, 155.12, 156.36, 158.03, 159.09, 161.07. Anal. Calcd for C$_{20}$H$_{26}$O$_5$: C, 69.34; H, 7.56. Found: C, 69.15; H, 7.93.

(+)-(8R,9S,10S)-10-Hydroxy-5-isopropyloxy-8,9-dimethyl-4-propyl-9,10-dihydro-8H-pyrano[2,3-f]-chromen-2-one (8a).

To a solution 7a (100 mg, 0.28 mmol) in THF (8 mL) and toluene (8 mL), maintained at −78° C., was added diethyl azodicarboxylate (DEAD, 0.455 mL, 2.88 mmol), PMe$_3$ (2.89 mL, 1.0M solution in THF), and chloroacetic acid[24] (220 mg, 2.32 mmol). The reaction mixture was stirred at −78° C. and allowed to warm to −30° C. over a period of 1.5 h (until complete disappearance of starting material was observed by TLC). Ammonium hydroxide (5 mL) was then added, and the solution was concentrated under reduced pressure. The residue obtained was then treated with ammonium hydroxide (5 mL) in CH$_3$CN (10 mL), and the mixture was stirred for 4 h. The mixture was then quickly extracted with ether, the organic layer was dried (MgSO$_4$), concentrated, and submitted for silica gel chromatography (Solvent A) to give 81 mg (81%) of 8a as a colorless syrup: [α]$_D^{20}$+106° (c 1.1, CHCl$_3$); $^1$H NMR (CDCl$_3$): δ0.99 (t, 3 H, J=7.3 Hz, —CH$_2$CH$_2$CH$_3$), 1.12 (d, 3 H, J=6.8 Hz, —CHCH$_3$), 1.38 and 1.40 [2d, 6 H, J=5.8 Hz, —CH(CH$_3$)$_2$], 1.42 [d, 3 H, J=6.5 Hz, —CH(CH$_3$)], 1.60 (m, 2 H, J=7.48 Hz, —CH$_2$CH$_2$CH$_3$), 1.93 (m, 1 H, H-9), 2.87 (m, 2 H, —CH$_2$CH$_2$CH$_3$), 3.59 (bs, 1 H, —OH), 3.91 (m, 1 H, H-8), 4.62 [m, 1 H, J=6.0 Hz, —CH(CH$_3$)$_2$], 4.70 (d, 1 H, J=7.6 Hz, H-10), 5.92 (s, 1 H, H-3), 6.21 (s, 1 H, H-6); $^{13}$C NMR (CDCl$_3$): δ 13.87, 15.73, 18.95, 21.66, 21.80, 23.19, 39.02, 40.48, 66.66, 70.77, 77.00, 96.92, 104.83, 106.14, 110.02, 155.69, 156.15, 157.75, 159.06, 160.48. Anal. Calcd for C$_{20}$H$_{26}$O$_5$.0.03CH$_2$Cl$_2$: C, 65.50; H, 7.21. Found: C, 65.74; H, 7.39.

(−)-7-Hydroxy-8-[(1S,2S)-1-hydroxy-2-methylbut-3-enyl]-5isopropyloxy-4-propyl-chromen-2-one [(−)-4a].

The procedure for compound 4 was repeated using (−)-(E)-25 crotyldiisopinocampheylborane8 to give −4a as a syrup: [α]$_D^{20}$−120° (c 1.0, CHCl$_3$); $^1$H NMR (CDCl$_3$): δ 0.99 (t 3 H, J=738 Hz, —CH$_2$CH$_2$CH$_3$), 1.05 (d, 3 H, J=6.89 Hz, —CHCH$_3$), 1.39 and 1.41 (2 d, 6 H, J=6.0 Hz, —CH (CH$_3$)$_2$), 1.59 (qt, 2 H, J=7.67 Hz, —CH$_2$CH$_2$CH$_3$), 2.64 (q, 1 H, J=7.41 Hz, —CHCH$_3$), 2.84 (bt, 2 H, J=7.78 Hz, —CH$_2$CH$_2$CH$_3$), 4.21 (bs, 1 H, —CHOH), 4.63 (m, 1 H, J=6.06, —CH(CH$_3$)$_2$), 5.05–5.2 (m, 2 H, —CH=CH$_2$), 5.38 (dd, 1 H, J=2.89 Hz, J=7.25 Hz, —CHOH), 5.82 (s, 1 H, H-3), 5.86–6.00 (m, 1 H, —CH=CH$_2$), 6.28 (s, 1 H, H-6), 9.57 (s, 1 H, Ar—OH); $^{13}$C NMR (CDCl$_3$): δ 13.91, 16.47, 21.79 (2C), 23.12, 38.98, 44.68, 70.72, 72.67, 98.04, 103.56, 105.77, 109.48, 117.07, 139.74, 153.38, 156.17, 159.54, 160.57, 161.36. Anal. Calcd for C$_{20}$H$_{26}$O$_5$: C, 69.34, H, 7.56. Found C, 69.22; H, 7.54.

(−)-7-Hydroxy-8-[(1S,2S)-1-tert-butyldimethylsilyloxy-2-methylbut-3-enyl]-5-isopropyloxy-4-propyl-chromen-2-one [(−)-5a].

By the procedure used for compound 5a, (−)-5a was obtained as a syrup: [α]D$^{20}$ −37 (c 1.0, CHCl$_3$); $^1$H NMR (CDCl$_3$): δ−0.03 (s, 3 H, —SiCH$_3$), 0.15 (s, 3 H, —SiCH$_3$), 0.88 (s, 9 H, —C(CH$_3$)$_3$, 0988 (d, 3 H, J=6.88 Hz, —CHCH$_3$), 1.01 (m, 3 H, —CH$_2$CH$_2$CH$_3$), 1.40 (m, 6 H, —CH(CH$_3$)$_2$), 1.63 (m, 2 H, —CH$_2$CH$_2$CH$_3$), 2.60 (q, 1 H, J=6.85 Hz, —CHCH$_3$), 2.87 (bt, 2 H, J=7.40 Hz, —CH$_2$CH$_2$CH$_3$), 4.63 (m, 1 H, J=5.9 Hz, —CH(CH$_3$)$_2$), 4.90–5.10 (m, 2 H. —CH═CH$_2$), 5.30 (d, 1 H, J=6.38 Hz, —CHOSi(CH$_3$)$_2$—), 5.86 (m, 1 H, —CH═CH$_2$), 5.90 (s, 1 H, H—3), 6.24 (s, 1 H, H-6), 9.16 (s, 1 H, ArOH); $^{13}$C NMR (CDCl$_3$): δ –0.35, –0.17, 13.89, 16.25, 18.04, 21.74, 21.83, 23.06, 25.66, 25.86, 38.94, 44.60, 70.65, 74.26, 97.52, 103.37, 106.55, 109.84, 115.69, 139.58. 152.96, 156.11, 158.93, 160.5, 160.73. Anal. Calcd for C$_{26}$H$_{40}$O$_5$Si: C, 67.78; H, 8.75. Found C, 67.90; H, 8.75.

(+)-(8R,9R,10R)-10-tert-Butyldimethylsilyloxy-5-isopropyloxy-8,9-dimethyl-4-propyl-9,10-dihydro-8H-pyrano[2,3-f]chromen-2-one [(–)-6a].

By the procedure used for compound 6, (–)-6a was obtained as a syrup: [α]$_D^{20}$+32° (c 1.0, CHCl$_3$); $^1$H NMR (CDCl$_3$): δ –0.10 (s, 3 H, —SiCH$_3$), 0.27 (s, 3 H, —SiCH$_3$), 0.81 (s, 9 H, —C(CH$_3$)$_3$), 0.99 (t, 3 H, J=7.3 Hz, —CH$_2$CH$_2$CH$_3$), 1.06 (d, 3 H, J=6.83 Hz, —CHCH$_3$), 1.3–1.42 (m, 9 H, —CH(CH$_3$)$_2$, —CHCH$_3$), 1.48–1.7 (m, 3 H, H-9, —CH$_2$CH$_2$CH$_3$), 2.89 (m, 2 H, —CH$_2$CH$_2$CH$_3$), 4.39 (m, 1 H, J=4.5 Hz, H-8), 4.59 (m, 1 H, J=5.9 Hz, —CH(CH$_3$)$_2$), 4.93 (bd, 1 H, J=2.2 Hz, —CHOSi(CH$_3$)$_2$—), 5.90 (s, 1 H, H-3), 6.19 (s, 1 H, H-6); $^{13}$C NMR (CDCl$_3$): δ –4.78, –4.63, 13.86, 14.16, 18.56, 19.26, 21.80, 21.88, 23.14, 26.03, 38.94, 39.23, 62.64, 70.62, 72.93, 96.59, 103.58, 106.67, 110.04, 154.23, 156.32, 158.07, 158.85, 160.80. MS (positive-ion FAB): m/z 461, [M+1]+, 417, 329. It is noteworthy, that although this compound is an intermediate in the production of the (–)-series of compounds, it showed a (+)-optical rotation.

(–)-(8S,9R,10S)-10-Hydroxy-5-isopropyloxy-8,9-dimethyl-4-propyl-9,10-di-hydro-8H-pyrano[2,3-f]-chromen-2-one[(–)-7a].

By the procedure used for compound 7, (–)-7a was obtained as a syrup: [α]$_D^{20}$–28° (c 1.1, CHCl$_3$); $^1$H NMR (CHCl$_3$): δ 0.98 (t, 3 H, J=7.36 Hz, —CH$_2$CH$_2$CH$_3$), 1.11 (d, 3 H, J=6.96 Hz, —CH(CH$_3$)), 1.38 [d, 9 H, J=5.94 Hz, —CHCH$_3$, —CH(CH$_3$)$_2$], 1.59 (m, 2 H, J=7.51 Hz, —CH$_2$CH$_2$CH$_3$), 1.73 (m, 1H, H-9), 2.90 (m, 2 H, —CH$_2$CH$_2$CH$_3$), 4.24 (m, 1 H, H-8), 4.61 (m, 1 H; J=5.9 Hz, —CH(CH$_3$)$_2$), 4.94 (bd, 1 H, J=2.98 Hz, H-10), 5.91 (s, 1 H, H-3), 6.16 (s, 1 H, H-6); $^{13}$C NMR (CDCl$_3$): δ 12.51, 13.86, 18.85, 21.70, 21.76, 23.17, 38.39, 38.90, 61.67, 70.66, 72.89, 96.66, 104.21, 106.21, 110.12, 155.13, 156.37, 158.04, 159.11, 161.08. Anal. Calcd for C$_{20}$H$_{26}$O$_5$ 0.22 H$_2$O: C, 68.56; H, 7.61. Found: C, 68.50; H, 7.62.

(–)-(8S, 9R, 10R)-10-Hydroxy-5-isopropyloxy-8,9-dimethyl-4-propyl-9,10-dihydro-8H-pyrano[2,3-f]-chromen-2-one [(–)-8a].

By the procedure used for compound 8, (–)-8a was obtained as a syrup: [α]$_D^{20}$ –90.7° (c 1.1, CHCl$_3$); $^1$H NMR (CDCl$_3$): δ 0.93 (t, 3 H, J=7.40 Hz, —CH$_2$CH$_2$CH$_3$), 1.07 (d, 3 H, J=6.8 Hz, —CH(CH$_3$)), 1.31 and 1.34 (2 d, 6 H, J=5.8 Hz, —CH(CH$_3$)$_2$), 1.37 (d, 3 H, J=6.55 Hz, —CH(CH$_3$)), 1.55 (m, 2 H, J=7.6 Hz, —CH$_2$CH$_2$CH$_3$), 1.85 (m, 1 H, J=8.61 Hz, H-9), 2.80 (m, 2 H, J=5.95 Hz, —CH$_2$CH$_2$CH$_3$), 3.50 (bs, 1 H, —OH), 3.85 (m, 1 H, J=6.4 Hz, H-8), 4.55 (m, 1 H, J=6.06 Hz, —CH(CH$_3$)), 4.64 (d, 1 H, J=7.64 Hz, H-10), 5.86 (s, 1 H, H-3), 6.15 (s, 1 H, H-6); $^{13}$C NMR (CDCl$_3$): δ 13.87, 15.12, 18.94, 21.65, 21.80, 23.19, 39.02, 40.47, 67.04, 70.76, 77.07, 96.91, 104.80, 106.13, 110.01, 155.77, 156.13, 157.89, 159.23, 160.44. Anal. Calcd for C$_{20}$H$_{26}$O$_5$: C, 69.34; H, 7.56. Found: C, 69.43; H, 7.39.

Resolution of Enantiomers in a Racemic Mixture

Racemic mixtures, such as 7b, 8b–8e, or others like those with substitution patterns as indicated in Table I, which are described herein, can be separated by means such as described in a recent treatise on the subject of stereochemistry.[27] While spontaneous crystallization methods, with or without additives, are always a possibility for separating enantiomers, the following two methods are considered more practical.

The enantiomers can be separated by chromatography over a chiral-phase column, i.e, one that utilizes a chiral stationary phase. The processes may be liquid-liquid, liquid-solid, gas-liquid, or gas-solid, with either liquid-liquid or liquid-solid modes being preferred. One such process has been described for resolution of the calanolides that uses amino acid (either D- or L- phenylglycine-bonded) supports.[28]

Other means of racemate resolution involves chemical resolution as diastereomers. Thus any number of optically active compounds could be used to derivatize the racemic mixtures, and the resulting diastereomeric derivatives are then separated by crystallization, chromatography, counter-current extraction, or by other means or combinations thereof, to give pure diastereomeric compounds of both enantiomers. Chemical processes, including but not limited to, hydrolysis and saponification by either chemical or enzymatic means, or other functional group removal methods then liberate each free enantiomer. These processes are especially well taught in the reference.[27]

Anti-HIV Activity

The compounds of the instant invention are useful to inhibit the growth or replication of a virus in a mammal. Examples of mammals include humans, primates, bovines, ovines, porcines, felines, canines, etc. Examples of viruses may include but are not limited to HIV-1, HIV-2, herpes simplex virus (types 1 and 2), varicella zoster virus, cytomegalovirus, papilloma virus, HTLV-1, HTLV-2, feline leukemia virus, avian sarcoma viruses such as rous sarcoma virus, hepatitis types A-E, influenza virus, measles, mumps and rubella viruses. More preferably, the compounds of the invention will be used to treat a human infected with a retrovirus (RT). Preferably the compounds of the present invention will be used to treat a human exposed or infected (i.e., in need of such treatment) with the human immunodeficiency virus, either prophylactically or therapeutically.

The compounds of the present invention are particularly useful in the prevention or treatment of infection by the human immunodeficiency virus and also in the treatment of consequent pathological conditions associated with AIDS. Treating AIDS is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected exposure to HIV by e.g., blood transfusion, exposure to patient blood during surgery or an accidental needle stick.

An advantage of certain compounds of the present invention is that they retain the ability to inhibit certain HIV RT mutants which are resistant to TiBO and other compounds known to inhibit RT. This is advantageous over the current AIDS drug therapy, where biological resistance often develops to nucleoside analogues used in the inhibition of RT.

The compounds of the invention may be assayed for antiviral activity via published protocols. They include, but are not limited to, cell count, cytopathic effect, dish-colony formation, microtiter-growth inhibition and thymidine incorporation. In addition, the compounds of the present invention can be assayed for their ability to inhibit HIV infection via an infectivity assay. The infectivity assay comprises infection of T-lymphocytes or macrocytes/macrophages with either HIV-1 or HIV-2. At six or more days post-infection, measurement of particle-associated reverse transcriptase activity and/or p24 antigen levels can be determined (see, for example, Clapham et al. *Nature*, 337:368–370 (1990) or McDougal et al., *J. Immun. Meth.*, 76:171–183 (1985)). In addition, the focal infectivity assay (FIA) can be used to assay the susceptibility of HIV to antiviral agents (see, e.g., Pincus et al., *BioTechniques*, 10:336–342 (1991).

Furthermore, the levels of antiviral "activity" of the compounds of the present invention can be rapidly determined in a series of interrelated assays via a semiautomated multiparameter approach as disclosed by Gulakowski et al., *J. Virol. Meth.* 33:87–100 (1991), which is incorporated herein by reference.

All compounds have activity to inhibit reverse transcriptase.

The compounds of this invention were also all assayed for activity in inhibiting the growth of HIV, human immunodeficiency virus, the virus known to cause AIDS. The protocol[25] was that of the National Cancer Institute (NCI) of the National Institutes of Health. The primary screen makes use of the HIV-1 strain of the virus. By this protocol, the procedure is as follows:

(1) The sample is dissolved in dimethyl sulfoxide, then diluted 1:100 in cell culture medium before preparing serial half-$\log_{10}$ dilutions. T4 lymphocytes (CEM cell line) are added, and after a brief interval, HIV-1 is added, resulting in a 1:200 dilution of the compound. Uninfected cells with the compound serve as a toxicity control, and infected and uninfected cells without the compound serve as basic controls.

(2) Cultures are incubated at 37° C. in a 5% carbon dioxide atmosphere for six days.

(3) The tetrazolium salt, XTT, is added to all wells, and cultures are incubated to allow formazan color development by viable cells.

(4) Individual wells are analyzed spectrophotometrically to quantitate fornazan production, and in addition are viewed microscopically for detection of viable cells and confirmation of protective activity.

(5) Drug-treated, virus-infected cells are compared with drug-treated, noninfected cells and with other appropriate controls (untreated infected and untreated noninfected cells, drug-containing wells without cells, etc.) on the same plate.

(6) Data are reviewed in comparison with other tests done at the same time, and a determination about activity is made.

The results are given for $IC_{50}$ and $EC_{50}$. $IC_{50}$ is a measure of "concentration for inhibition of 50% of cell growth" and is measured from drug-treated, uninfected cells, thus giving a measure of drug toxicity toward T4 lymphocytes. The $EC_{50}$ is "effective inhibition for 50% of cell growth" and is measured on drug-treated, HIV-infected cells. A ratio of these values, $IC_{50}/EC_{50}$ gives the therapeutic index, a measure of the overall effectiveness of the drug in halting virus-infested cell growth. Typically for anti-HIV drugs to be classed as "active" in the NCI protocol, the $IC_{50}$ value should be at least micromolar ($10^{-6}$M) and the $EC_{50}$ value should be sub-micromolar ($10^{-7}$M or lower); however, these values are only ideal, and may vary a log-order in magnitude or more. Some potent, active anti-HIV drugs show typically $IC_{50}$ values of $10^{-5}$M, with $EC_{50}$ values of $10^{-6}$M. TI values should be $10^1$ to $10^2$ or higher (the higher the value, the more potent the drug). Large, positive TI values, measured in the $10^2$–$10^3$ range indicate a potent, relatively nontoxic drug and represent the near-ideal drug candidate. The classifications, "Active," "Moderately Active," and "Inactive" are made using the Weislow assay with the criteria set forth in NCI protocol.

The results for epimers 8a and (−)-8a, i.e., the compounds of the calanolide A series and for epimers (−)-7 and (+)-7, both of the calanolide B series where the 2,2-dimethyl-2H-pyran ring system had been replaced by a 5-O-isopropoxy group, consistently showed impressive results in the anti-HIV screen as described in the above protocol. Typical results are shown in Table 3.

In comparing the family of diastereomers, i.e., 7a and (−)-7a with 8a and (−)-8a, the (−)-7a and 8a compounds were the more potent. Compounds (−)-8a and 7a were both labeled "inactive" in the highly demanding NCI protocol.

In screening tests for RT binding activity, these as well as the other compounds which are reported to be not as active as the best compounds, are nonetheless active in assays for RT activity.

TABLE 3

Anti-HIV Activity of Compounds of Types 7 and 8[a]

| Compound | $IC_{50}$ (M) | $EC_{50}$ (M) | TI | Classification |
|---|---|---|---|---|
| 7a | 8.40 E-6 | — | — | Inactive |
| (−)-7a | 8.11 E-6 | 9.63 E-7 | 84.2 | Active |
| 8a | 2.10 E-5 | 1.61 E-7 | 130 | Active |
| (−)-8a | 7.34 E-6 | — | — | Inactive |
| 8b[b] | >2.0 E-4 | — | — | Inactive |
| 8c[b] | 3.74 E-5 | 3.66 E-6 | 10.2 | Mod. Active |
| 8d[b] | 9.66 E-6 | 4.74 E-6 | 2.04 | Mod. Active |
| 8e[b] | 8.34 E-6 | — | — | Inactive |

[a] Testing was conducted according to NCI's protocol [Weislow, O. W. et al. J. Natl. Cancer Inst. 1989, 81, 577–586]. The virus strain was HIV-1, and the cell line was CEM-SS.
[b] Testing was carried out on the racemic drug.

The activities for (−)-7a and 8a are remarkable in that they were totally unexpected. For example, the 5-O-methyl (8b), the 5-O-sec-butyl (8c), the 5-O-allyl (8d), and the 5-O-propargyl (8e) analogues, all showed less potent activities (see Table 3). Compounds 8c and 8d were considered "moderately active". This result shows essentially parallel structure-activity relationships that were established for the known calanolides, (+)-calanolide A and (−)-calanolide B being the more potent of the four diastereomers in that series.[26] Not until the 5-O-isopropyl derivatives (−)-7a and 8a were evaluated in the HIV screen were these remarkable activities discovered.

It is to be noted that the term "inactive" refers only to the response to the Weislow test. These compounds are active in screening tests for inhibition of reverse transcriptase.

Noteworthy is that the 5-O-isopropyl derivatives (−)-7a and 8a have shown potent inhibitory activities against strains of the HIV virus that are resistant to other drugs that inhibit the HIV reverse transcriptase enzyme. Among these are the following strains of the virus: (1) HIV-1 (6R), an AZT-resistant strain; (2) N119, a nevirapine-resistant strain bearing a mutation at AA codon 181; (2) DPS, a diphenyl sulfone-resistant strain bearing a different mutation at AA codon 181.

These activities are shown in Table 4. From the data in the Table, both compounds (−)-7a and 8a were classified as "active" for inhibition of each resistant HIV strain. From the large TI values, their potencies against these resistant strains of the virus are novel and remarkable. Other compounds of the invention are expected also to have this property.

TABLE 4

Activities of (−)-7a and 8a Against Strains of HIV that are Resistant to Other Inhibitors of HIV Reverse Transcriptase[a]

| Compound | HIV Strain | IC$_{50}$ (M) | EC$_{50}$ (M) | TI | Classification |
|---|---|---|---|---|---|
| (−)7a | HIV-1 (6R) | 1.08 E-5 | 6.39 E-7 | 16.9 | Active |
|  | N119 | 1.11 E-5 | 7.01 E-9 | 1540 | Active |
|  | DPS | 1.20 E-5 | 9.90 E-8 | 121 | Active |
| 8a | HIV-1 (6R) | >2.0 e-5 | 3.65 E-7 | 54.8 | Active |
|  | N119 | >2.0 E-5 | 6.35 E-9 | — | Active |
|  | DPS | >2.0 E-5 | 6.49 E-8 | >308 | Active |

[a] Testing was conducted according to NCI's protocol [Weislow, O. W. et al. J. Natl. Cancer Inst. 1989, 81, 577–586]. The virus strain was HIV-1, and the cell line was MT-4.

It is apparent from the teaching of this disclosure that a principal objective of the invention was to find compounds that exhibit very high activity in the Weislow protocol. Such have indeed been found. However, numerous compounds other than those that excel in that respect, are expected to have biological activity that may make them interesting candidates for biological applications other than as anti-HIV drugs.

Pharmaceutical Compositions

Pharmaceutical compositions of the compounds of the present invention may be formulated, as is well known in the prior art, such as by reference to such materials as in well known compilations as *Remington's Pharmaceutical Sciences*, Mack Publishing Co., Easton, Pa., USA.

The dosage ranges for administration of the compounds of the present invention are those to produce the desired affect without undue toxicity, whereby symptoms of infection are ameliorated.

The pharmaceutical composition may contain other pharmaceuticals in conjunction with the compounds of the instant invention, to treat (therapeutically or prophylactically) acquired immunodeficiency syndrome (AIDS). For example, other pharmaceuticals may include, but are not limited to, other antiviral compounds (e.g., AZT, ddC, TiBO derivatives, acyclovir, α-interferon), immunostimulants (e.g., various interleukins and cytokines), immunomodulators and antibiotics (e.g., antibacterial, antifungal, anti-pneumocysitis agents), even when they do not show potent activity in the NCI Weislow protocol.

In addition, the compounds of the invention are useful as tools and/or reagents to study inhibition of retroviral reverse transcriptases. For example, the compounds selectively inhibit HIV reverse transcriptase. Hence, the compounds are useful as an SAR (structure-activity relationships) tool to study, select and/or design other molecules to inhibit HIV.

The active compounds described in this patent are potentially useful as chemotherapeutic agents for limiting the proliferation of the HIV virus in man. These compounds may be used either alone or in combination with other nucleoside and non-nucleoside anti-HIV agents. Especially promising are compounds (−)-7a and (+)-8a, whose activities are remarkable among the congeners of the invention. Furthermore, (−)-7a and (+)-8a show potent activity against strains of HIV that are resistant to other drugs which are either in clinical use or under development for clinical use. Thus combination therapy with one or more of these agents provides an attractive regimen to halt proliferation of HIV under clinical conditions. These agents include, but are not restricted to, inhibitors of HIV reverse transcriptase, e.g., AZT (zidovudine, Retrovir®), ddI (dideoxyinosine, didanosine, Videx®), d4T (dideoxydidehydrothymidine, stavudine), ddC (dideoxycytidine, zalcitabine), and nevirapine, among others. Combination regimens with HIV protease inhibitors might include, but are not restricted to, e.g., ritonavir (Norvir®) or saquinavir mesylate (Invirase®), among other drugs.

The preferred route of administration is oral, although other routes of administration are acceptable. The compounds may be mixed with inert materials for pharmaceutical efficacy. Among these are syrups, for administration as a palatable liquid; buffer salts, e.g., magnesium hydroxide, aluminum hydroxide, calcium carbonate, or other regimen that serves to limit stomach acidity; certain components, e.g., insoluble salts, that facilitate compounding the drugs into tablets, powders, or other forms for oral administration; the compounds may be formulated, generally admixed with an inert carrier, in gelatin or similar capsules. The compounds may be admixed with gels, waxes, or other components and formulated as suppositories; other forms include lozenges and orally soluble tablets. The compounds may be formulated in aqueous solution for intravenous (i.v.), intraperitoneal (i.p.), or subcutaneous (s.c.) administration. Topical applications include mixtures of the compounds with oils or fatty acid esters or as components of skin patches that are capable of delivering the drugs across the dermal layer. Aqueous solutions, or solutions in suitable carriers, could be administered intranasally.

The compounds of the invention readily lend themselves to being made part of what are called "inclusion compounds", such as with cyclodextrans and other suitable substances.

All publications referenced herein are hereby incorporated by reference in their entireties.

The invention is not limited to the embodiments described herein, but encompasses all modifications with the scope of the art of the following claims.

The invention is defined in the claims which appear below.

References:

1. (a) Kashman, Y.; Gustafson, K. R.; Fuller, R. W.; Cardellina, J. H., II; McMahon, J. B.; Currens, M. J.; Buckheit, R. W., Jr.; Hughes, S. H.; Cragg, G. M.; Boyd, M. R. *J. Med. Chem.* 1992, 35, 2735–2743. (b) Fuller, R. W.; Bokesh, H. R.; Gustafson, K. R.; McKee, T. C.; Cardellina, J. H., II; McMahon, J. B.; Cragg, G. M.; Soejarto, D. D.; Boyd, M. R. *Bioorg. Med. Chem. Lett.* 1994, 4, 1961–1964. (c) Newman, R. A.; Costa, M.; Cisneros, A. J. *J. Chromatogr. B* 1994, 658, 129–133. (d) Palmer, C. J.; Josephs, J. L. *Tetrahedron Lett.* 1994, 35, 5363–5366. (e) Cardellina, J. H.; Bokesch, H. R.; Mckee, T. C.; Boyd, M. R. *Bioorg. Med. Chem. Lett.* 1995, 5, 1011–1014. (f) Kucherenko, A.; Flavin, M. T.; Boulanger, W. A.; Khilevich, A.; Shone, R. L.; Rizzo, J. D.; Sheinkman, A. K. *Tetrahedron Lett.* 1995, 36, 5475–5478. (g) Flavin, M. T.; Rizzo, J. D.; Khilevich, A.; Sheinkman, A. K.; Vilaychack, V.; Lin, L.; Chen, W.; Greenwood, E. M.; Pengsuparp, T.; Pezzuto, J. M.; Hughes, S. H.; Flavin, T. M.; Cibulski, M.; Boulanger, W. A.; Shone, R. L.; Xu, Z. Q. *J. Med. Chem.* 1996, 39, 1303–1313.

2. Gallo, R. C.; Montagnier, L. *Sci. Amer.* 1988, 259, 41–48.

3. Deshpande, P. P.; Tagliaferri, F. ; Victory, S. F.; Yan, S.; Baker, D. C. *J. Org. Chem.* 1995, 60, 2964–2965.

4. PCT International publication WO 94/2800, published December 1994; PCT publication WO 94/14789 published July 1994; and PCT publication WO 93/20082, published December 1993. Also, see Galinis, D. L.; Fuller, R. W.; McKee, T. C.; Cardellina, J. H. II; Gulakowski, R. J.; McMahon, J. B.; and Boyd, M. R., "*J. Med. Chem.,* 1996, 4507–4510.

5. Patil, A. D.; Freyer, A. J.; Eggleston, D. S.; Haltiwanger, R. C.; Bean, M. F.; Taylor, P. B.; Caranfa, M. J.; Breen, A. L.; Bartus, H. R.; Johnson, R. K.; Hertzberg, R. P.; Westley, J. W. *J. Med. Chem.* 1993, 36, 4131–4138.

6. Chenera, B.; West, M. L.; Finkelstein, J. A.; Dreyer, G. B. *J. Org. Chem.* 1993, 58, 5605–5606.

7. Mitsunobu, O. *Synthesis,* 1981, 1–28.

8. Brown, H. C.; Bhat, K. S. *J. Am. Chem. Soc.* 1986, 108, 5919–5923.

9. Vilsmeier, J. C. *Adv. Org. Chem.* 1976, 9, 225–342.

10. Crounse, N. N. *Org. Reactions* 1949, 5, 290–300.

11. Truce, W. E. *Org. Reactions* 1957, 9, 38–72.

12. See for example, Vogel, A. I. *J. Chem. Soc.* 1948, 616–611.

13. Brown, H. C.; Jadhav, P. K.; Mandal, A. K. *J. Org. Chem.* 1982, 47, 5074–5083.

14. Jadav, P. K.; Kulkarni, *J. Heterocycles* 1982, 18, 169.

15. Brown, H. C.; Vara Prasad, J. V. N.; Zaidlewicz, M. *J. Org. Chem.* 1988, 53, 2911–2916.

16. de Richter, R. K.; Bonato, M.; Follet, M.; Kamenka, J. M. *J. Org. Chem.* 1990, 55, 2855–2860.

17. Jadhav, P. K.; Brown, H. C. *J. Org. Chem.* 1981, 46, 2988–2990.

18. Kabalka, G. W.; Shoup, T. M.; Goudgaon, N. M. *J. Org. Chem.* 1989, 54, 5930–5933.

19. Rama Rao, A. V.; Gaitonde, A. S.; Prakash, K. R. C.; Prahlada Rao, S. *Tetrahedron Lett.* 1994, 35, 6347–6350.

20. Rogers, S. M. *Preparative Biotransformations,* Wiley: New York, 1993, chapter 2.

21. Ishikawa, T.; Oku, Y.; Kotake, K.-I.; Ishii, H. *J. Org. Chem.* 1996, 61, 6484–6485.

22. Gemal, A. L.; Luche, J.-L. *J. Am. Chem. Soc.* 1981, 103, 5454–5459.

23. Schaumberq, J. P.; Hokanson, G. C.; French, J. C.; Smal, E.; Baker, D. C. *J. Org. Chem.* 1985, 50, 1651–1656.

24. Saïah, M.; Bessodes, M.; Antonakis, K. *Tetrahedron Lett.* 1992, 33, 4317–4320.

25. Weislow, O. W. et al. *J. Natl. Cancer Inst.* 1989, 81, 577–586

26. References 1e and 4, hereinabove.

27. Eliel, E. L.; Wilen, S. H. *Stereochemistry of Organic Compounds,* Wiley; New York, 1994, Chapter 7.

28. References 1(a)–(c), hereinabove.

I claim:

1. An optically active pyran-chromenone compound of either one of the A or B series of the formula

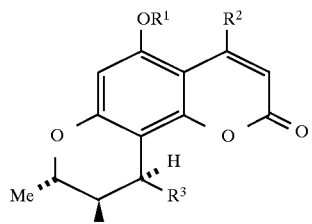

B Series

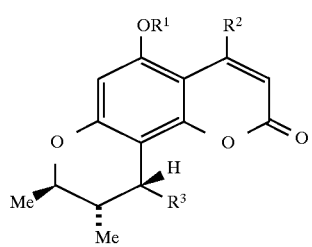

A Series in which $R^1$ is straight or branched alkyl of not more than 6 carbon atoms, cycloalkyl of not more than 8 carbon atoms, allyl, alkenyl wherein the alkyl has not more than 6 carbon atoms, alkaryl wherein the aryl has not more 6 carbon atoms, $R^2$ is hydrogen, straight or branched alkyl, cycloalkyl or aryl wherein the alkyl or aryl is of not more than 6 carbon atoms and $R^3$ is hydroxyl or keto.

2. The compound of claim 1 in which $R^1$ is isopropyl, sec-butyl or allyl, $R^2$ is 1-propyl and $R^3$ is hydroxyl.

3. The compound of claim 2 in which $R^1$ is isopropyl.

4. The compound of claim 3 in which $R^2$ is 1-propyl.

5. The compound of claim 1 wherein $R^1$ is branched alkyl of not more than 6 carbon atoms selected from 1-methylpropyl, 1-methylpentyl, 2-methylpentyl, 1,1-dimelhylpropyl, and 1,1-dimethylethyl.

6. The compound of claim 1 wherein the stereochemistry is as follows:

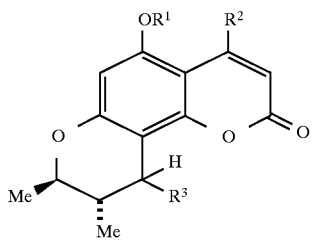

wherein $R^1$ is isopropyl, $R^2$ is propyl and $R^3$ is hydroxyl.

7. The compound of claim 1 wherein the stereochemistry is as follows:

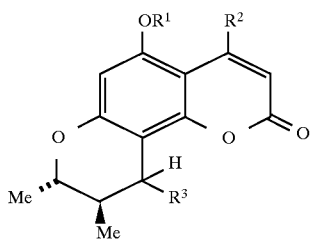

wherein $R^1$ is isopropyl, $R^2$ is 1-propyl and $R^3$ is isopropyl.

8. The chromenone compound of claim 6 which is compound (+)-8a of the A series.

9. The chromenone compound of claim 7 which is compound (−)-7a of the B series.

10. The 10-carbon epimer of the compound of claim 8, which is the (+)-7a compound.

11. The 10-carbon epimer of the compound of claim 9, which is the (−)-8a compound.

12. The fused pyran-chromenone of the structure

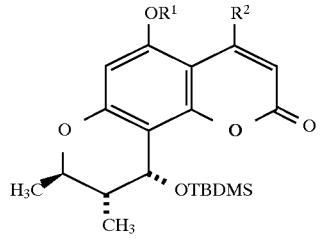

wherein $R^1$ is lower alkyl, allyl, or propargyl $R^2$ is 1-propyl and OTBDMS is OSiMe$_2$tert-butyldimethylsilane or tert-butyldimethylsilane.

13. The fused pyran-chromenone of claim 12 which is the 6a compound wherein $R^1$ is isopropyl.

14. The homoallylic compounds of the structure

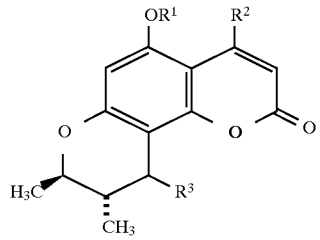

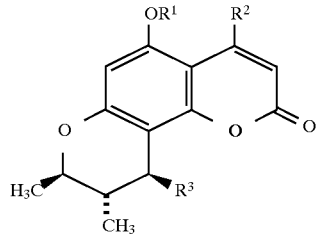

wherein $R^1$ is lower alkyl, allyl, or propargyl, $R^2$ is 1-propyl and.

15. The homoallylic compound of claim 14 which is the 6a or 7a compounds, wherein the alkyl is isopropyl.

16. The 8-methyl-10-pyranones of the structure

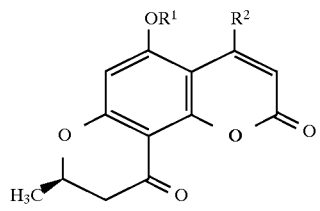

wherein $R^1$ is isopropyl, allyl, or propargyl and $R^2$ is 1-propyl.

17. The trans-8,9-dimethylpyranone compounds of the structure

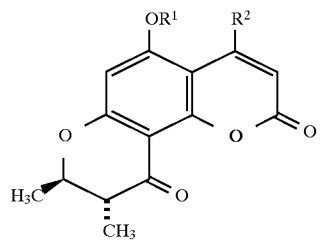

wherein $R^1$ is isopropyl, allyl, or propargyl and $R^2$ is 1-propyl.

18. A pharmaceutical composition which comprises a pharmaceutically acceptable carrier and in a nontoxic effective amount, a pyran-chromenone of the formula

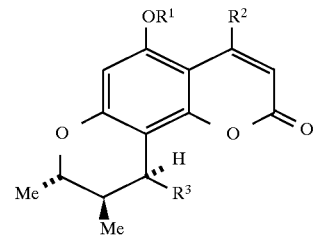

B Series

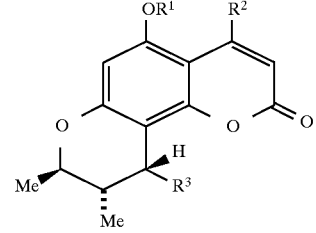

A Series or a pharmaceutically acceptable salt thereof, in which $R^1$ is straight or branched alkyl of not more than 6 carbon atoms, cycloalkyl of not more than 8 carbon atoms, allyl, alkenyl wherein the alkyl has not more than 6 carbon atoms, alkaryl wherein the aryl has not more than 6 carbon atoms, $R^2$ is hydrogen, straight or branched alkyl, cycloalkyl or aryl wherein the alkyl or aryl is of not more than 6 carbon atoms and $R^3$ is hydroxyl or keto.

19. The pharmaceutical composition of claim 18 in which in the compound $R^1$ is isopropyl, sec-butyl or allyl, $R^2$ is 1-propyl and $R^3$ is hydroxyl.

20. The pharmaceutical composition of claim 19 in which in the compound $R^1$ is isopropyl.

21. The pharmaceutical composition of claim 20 in which in the compound $R^2$ is 1-propyl.

22. The pharmaceutical composition of claim 18 in which $R^1$ is branched alkyl of not more than 6 carbon atoms selected from 1-methylpropyl, 1-methylpentyl, 2-methylpentyl, 1,1-dimethylpropyl, and 1,1-dimethylethyl.

23. The pharmaceutical composition of claim 18, wherein the stereochemistry of the compound is as follows:

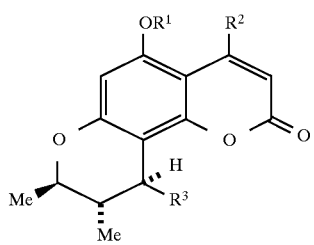

wherein R¹ is isopropyl, R² is propyl and R³ is hydroxyl.

24. The pharmaceutical composition of claim 18, wherein the stereochemistry of the compound is as follows:

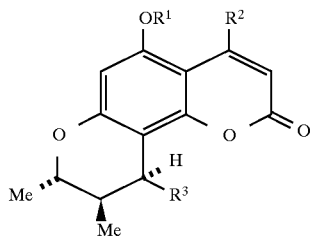

wherein R¹ is isopropyl, R² is 1-propyl and R³ is hydroxyl.

25. The pharmaceutical composition of claim 23 in which the compound has the structure

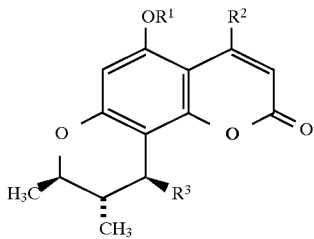

(a) one or more of the following inhibitors of HIV transcriptase: AZT, ddI, d4T, ddC or nevirapine and (b) one or more of the following protease inhibitors: ritonavir or saquinavir mesylate.

26. The pharmaceutical composition of claim 24 in which the compound has the structure

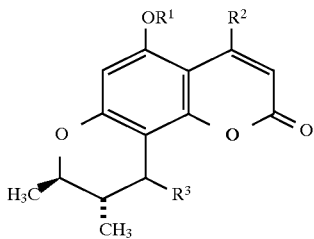

(a) one or more of the following inhibitors of HIV transcriptase: AZT, ddI, d4T, ddC or nevirapine, and (b) one or more of the following protease inhibitors: ritonavir or saquinavir mesylate.

27. The pharmaceutical composition of claim 18 which comprises in addition (a) one or more of the following inhibitors of HIV transcriptase: AZT, ddI, d4T, ddC or nevirapine, and
(b) one or more of the following protease inhibitors: ritonavir or saquinavir mesylate.

28. A method for treating or preventing a viral infection, which method comprises administering to a human an antiviral, nontoxic amount of at least one pyran-chromenone of the formula

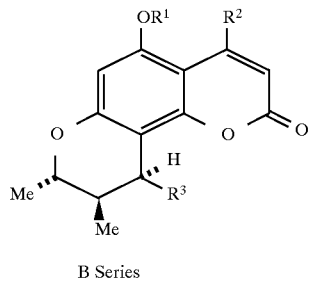

B Series

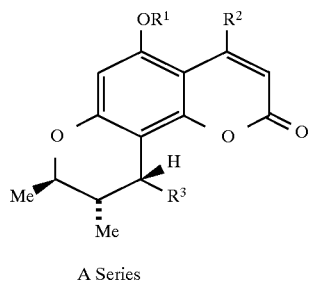

A Series in which R¹ is straight or branched alkyl of not more than 6 carbon atoms, cycloalkyl of not more than 8 carbon atoms, allyl, alkenyl wherein the alkyl has not more than 6 carbon atoms, alkaryl wherein the aryl has not more than 6 carbon atoms, R² is hydrogen, straight or branched alkyl, cycloalkyl or aryl wherein the alkyl or aryl is of not more than 6 carbon atoms and R³ is hydroxyl or keto.

29. The method of claim 28 in which together with, before or after the administration of said compound, there is administered at least one additional antiviral or protease inhibitor compound.

30. The method of claim 29 in which the additional antiviral compound is AZT, ddI, d4T, ddC, nevirapine, ritonavir or saquinavir mesylate.

31. The method of claim 30 wherein the viral infection is a retroviral infection by an HIV virus that is resistant to drugs that inhibit the HIV reverse transcriptase enzyme (HIV RT).

32. The method of claim 31 wherein the resistant viral strain is HIV-1 (6R), DPS or N119.

33. The pharmaceutical composition of claim 19, 20, 21, 22, 23 or 24 wherein the composition further comprises (a) one or more of the following inhibitors of HIV transcriptase: AZT, ddI, d4T, ddC or nevirapine, and (b) one or more of the following protease inhibitors: ritonavir or saquinavir mesylate.

* * * * *